US008912000B2

(12) United States Patent
Daniel et al.

(10) Patent No.: US 8,912,000 B2
(45) Date of Patent: Dec. 16, 2014

(54) DOWNHOLE MASS SPECTROMETRIC HYDROCARBON DETERMINATION IN PRESENCE OF ELECTRON AND CHEMICAL IONIZATION

(75) Inventors: Pierre J. Daniel, Missouri City, TX (US); Julian J. Pop, Houston, TX (US); Reza Taherian, Sugar Land, TX (US); Bruno Drochon, Cambridge (GB)

(73) Assignee: Schlumberger Technology Corporation, Sugar Land, TX (US)

( * ) Notice: Subject to any disclaimer, the term of this patent is extended or adjusted under 35 U.S.C. 154(b) by 774 days.

(21) Appl. No.: 13/054,118

(22) PCT Filed: Jul. 17, 2009

(86) PCT No.: PCT/US2009/051016
§ 371 (c)(1), (2), (4) Date: Apr. 6, 2011

(87) PCT Pub. No.: WO2010/009411
PCT Pub. Date: Jan. 21, 2010

(65) Prior Publication Data
US 2011/0189778 A1 Aug. 4, 2011

Related U.S. Application Data
(60) Provisional application No. 61/081,621, filed on Jul. 17, 2008.

(51) Int. Cl.
*G01N 33/24* (2006.01)
*E21B 49/08* (2006.01)
*H01J 49/14* (2006.01)

(52) U.S. Cl.
CPC .................................... *H01J 49/145* (2013.01)
USPC ...... 436/28; 73/19.09; 73/152.03; 73/152.04; 73/152.55; 166/264; 250/253; 250/254; 250/255; 250/256; 250/281; 250/282; 250/285; 436/25; 436/29; 436/30; 436/32; 436/139; 436/173

(58) Field of Classification Search
USPC ......... 436/25, 28–30, 32, 139, 173; 73/19.09, 73/152.03–152.04, 152.55; 166/264; 250/253–256, 281–282, 285
See application file for complete search history.

(56) References Cited

U.S. PATENT DOCUMENTS 2,324,085 A * 7/1943 Horvitz et al. .................. 436/32
3,033,287 A * 5/1962 Bond ....................... 166/250.16
(Continued)

FOREIGN PATENT DOCUMENTS

GB 2388658 11/2003
WO 2004048969 6/2004

OTHER PUBLICATIONS

Stevenson, D. P. et al, Journal of the American Chemical Society 1942, 64, 1588-1594.*

(Continued)

*Primary Examiner* — Arlen Soderquist
(74) *Attorney, Agent, or Firm* — Cathy Hewitt; Kenneth L. Kincaid

(57) ABSTRACT

Methods and apparatus for obtaining a mass spectrum of a sample and determining a concentration of a component of the sample by utilizing a model of chemical and electron ionization and the obtained mass spectrum.

20 Claims, 17 Drawing Sheets

(56) References Cited

U.S. PATENT DOCUMENTS

| | | | | |
|---|---|---|---|---|
| 4,266,127 | A * | 5/1981 | Chang | 250/288 |
| 4,377,745 | A * | 3/1983 | Chang | 250/283 |
| 4,547,691 | A | 10/1985 | Valdois et al. | |
| 4,739,654 | A | 4/1988 | Pilkington et al. | |
| 4,771,172 | A * | 9/1988 | Weber-Grabau et al. | 250/282 |
| 4,833,915 | A | 5/1989 | Radd et al. | |
| 4,887,464 | A | 12/1989 | Tannenbaum et al. | |
| 4,975,576 | A * | 12/1990 | Federer et al. | 250/282 |
| 5,055,677 | A * | 10/1991 | Amirav et al. | 250/282 |
| 5,090,256 | A | 2/1992 | Issenmann | |
| 5,101,105 | A * | 3/1992 | Fenselau et al. | 250/281 |
| 5,306,909 | A | 4/1994 | Jones et al. | |
| 5,394,345 | A | 2/1995 | Berard et al. | |
| 5,453,613 | A * | 9/1995 | Gray et al. | 250/281 |
| 6,443,001 | B1 | 9/2002 | Duriez et al. | |
| 6,627,873 | B2 | 9/2003 | Tchakarov et al. | |
| 6,661,000 | B2 | 12/2003 | Smith et al. | |
| 6,670,605 | B1 | 12/2003 | Storm, Jr. et al. | |
| 7,002,142 | B2 | 2/2006 | Mullins et al. | |
| 7,075,063 | B2 | 7/2006 | Dong et al. | |
| 7,114,562 | B2 | 10/2006 | Fisseler et al. | |
| 7,153,694 | B2 * | 12/2006 | Evans et al. | 436/139 |
| 7,318,343 | B2 | 1/2008 | Coenen | |
| 7,337,660 | B2 * | 3/2008 | Ibrahim et al. | 73/152.55 |
| 7,379,180 | B2 | 5/2008 | Vannuffelen et al. | |
| 7,458,257 | B2 * | 12/2008 | Pop et al. | 73/152.04 |
| 7,791,042 | B2 * | 9/2010 | McCauley et al. | 250/427 |
| 2003/0180963 | A1 * | 9/2003 | Evans et al. | 436/139 |
| 2004/0014223 | A1 | 1/2004 | Audibert et al. | |
| 2006/0224333 | A1 | 10/2006 | Frechin et al. | |
| 2008/0110253 | A1 | 5/2008 | Stephenson et al. | |
| 2008/0111064 | A1 | 5/2008 | Andrews et al. | |
| 2008/0141767 | A1 | 6/2008 | Raghuraman et al. | |
| 2008/0257036 | A1 | 10/2008 | Chaudoreille et al. | |
| 2009/0030858 | A1 * | 1/2009 | Hegeman et al. | 706/17 |
| 2009/0049889 | A1 * | 2/2009 | Pop et al. | 73/19.09 |
| 2010/0181471 | A1 * | 7/2010 | Pop et al. | 250/254 |

OTHER PUBLICATIONS

Munson, M. S. B. et al, Journal of the American Chemical Society 1965, 18, 3294-3299.*

Houriet, R. et al, Journal of the American Chemical Society 1977, 99, 3599-3602.*

Kim, J. K. et al, Journal of Physical CHemistry 1977, 81, 1798-1805.*

Harvey, T. M. et al, in "Monitoring Toxic Substances" American Chemical Society Symposium Series 1979, 195-216, Schuetzle, D. editor, American CHemical Society, Washington, D.C.*

Poppe, A. et al, Organic Mass Spectometry 1986, 21, 59-62.*

Cairns, T. et al, Rapid Communications in Mass Spectromtery 1992, 6, 331-338.*

Cairns, T. et al, Rapid Communications in Mass Spectromtery 1992, 6, 449-453.*

Dong, C. et al., New Downhole Fluid Analyzer Tool for Improved Reservoir Characterization, SPE 108566, Aberdeen, Scotland, U.K., Sep. 4-7, 2007.

Mullins, Oliver C. et al., Oil Reservoir Characterization via Crude Oil Analysis by Downhole Fluid Analysis in Oil Wells with Visible-Near-Infrared Spectroscopy and by Laboratory Analysis with Elctrospray Ionization Fourier Transform Ion Cyclotron Resonance Mass Spectroscopy, Energy & Fuels 2006, 20, pp. 2448-2456.

Freifeld, B.M. et al., Real-Time Quadrupole Mass Spectrometer Analysis of Gas in Borehole Fluid Samples Acquired Using the U-Tube Sampling Methodology, Geofluids 2006, vol. 6, pp. 217-224.

Kandel, D. et al., Improved Integrated Reservoir Interpretation Using the Gas While Drilling (GWD) Data, SPE 65176, Paris, France, Oct. 24-25, 2000, pp. 1-17.

Edman, J.D. et al., Geochemistry in an Integrated Study of Reservoir Compartmentalization at Ewing Bank 873, Offshore Gulf of Mexico, SPE Reservoir Eval. & Eng. 2 (6), Dec. 1999, pp. 520-526.

Blanc, P. et al, Reducing Uncertainties in Formation Evaluation through Innovative Mud Logging Techniques, SPE 84383, Denver, Colorado, Oct. 5-8, 2003, pp. 1-19.

Brumboiu, A.O. et al., Application of Semipermeable Membrane Technology in the Measurement of Hydrocarbon Gases in Drilling Fluids, SPE 62525, Long Beach, California, Jun. 2000, pp. 1-12.

Breviere, et al. "Gas Chromatography-Mass Spectroscopy (GCMS) — A New Wellsite Tool for Continuous C1-C8 Measurement in Drilling Mud — Including Original Gas extractor and Gas line Concepts. First results and Potential", paper presented at the SPWLA 43rd Annual Logging Symposium, Jun. 2-5, 2002.

McKinney, et al. "Advanced Mud Gas Logging in Combination with Wireline Formation Testing and Geochemical Fingerprinting for an Improved Understanding of Reservoir Architecture," SPE-109861-MS, SPE Annual Technical Conference and Exhibition, Anaheim, California, Nov. 11-14, 2007.

International Search Report and Written Opinion for International Application No. PCT/US2009/051016 dated Feb. 10, 2010.

Ellis, et al. "Mud gas Isotope Logging (MGIL) Assists in Oil and Gas Drilling operations", Oil and Gas Journal, May 26, 2003, pp. 32-41.

Haworth, et al. "Interpretation of Hydrocarbon Shows Using Light (C1-05) Hydrocarbon Gases from Mud-Log Data", AAPG Bulletin, vol. 69, No. 8, 1985, pp. 484-485.

* cited by examiner

DOWNHOLE MASS SPECTROMETRIC HYDROCARBON DETERMINATION IN PRESENCE OF ELECTRON AND CHEMICAL IONIZATION

CROSS-REFERENCE TO RELATED APPLICATIONS

This application claims the benefit of U.S. Provisional Application No. 61/081,621, entitled "METHOD FOR DETERMINING HYDROCARBON IN PRESENCE OF ELECTRON AND CHEMICAL IONIZATION," filed Jul. 17, 2008, the disclosure of which is hereby incorporated herein by reference.

BACKGROUND OF THE DISCLOSURE

When performing mud gas logging at the surface of a drilling site, one method of analyzing the gas onsite is the combined use of a gas chromatograph and a mass spectrometer. From this analysis, indicators such as "wetness" (W), "balance" (B) and "character" (C) can be calculated. These indicators provide information about the maturity and nature of hydrocarbons comprising the source of the oil accumulation, compartmentalization of the reservoir being drilled, and oil quality, as well as information regarding production zones, lithology changes, history of a reservoir accumulation, or seal effectiveness.

However, surface mud gas logging has intrinsic limitations, such as contamination of the gas sample at the surface by air requiring the use of strict quality control procedures, or sampling contamination caused by fluids from previously drilled layers. Furthermore, such measurements are intrinsically inaccurate because the depth of the sampling location is inferred from gross measurements of mud transit time and average mud velocity.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1:
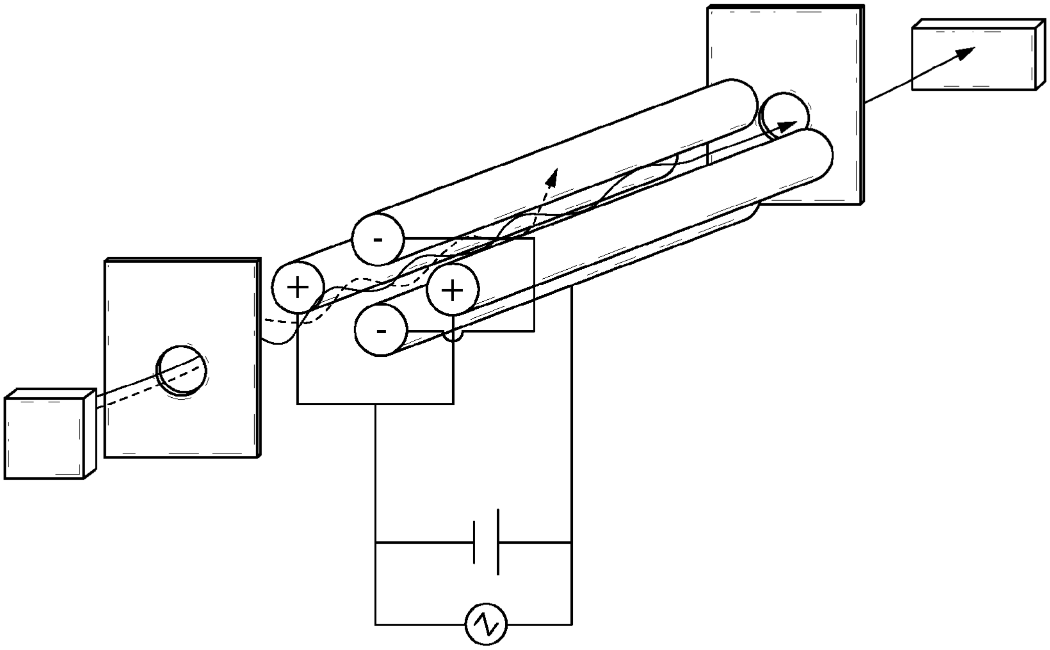
FIG. 1 (Prior Art)
FIG. 1 is a schematic view of prior art apparatus.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

One or more aspects of the present disclosure may effectively extend the range of measurements taken downhole, and/or may allow performing the measurements close to the bit so that the depth information is not lost. For example, sampling fluid at the bit level may be pursued as a means to eliminate the contamination dependency and improve real-time decision processes. Through real-time accurate information, geosteering, well placement, reservoir mapping and continuity may be better achieved.

One or more aspects of the present disclosure also regard standalone mass spectrometry as a means to measure fluid properties downhole at the bit localization. Methane and isobutane gases, present downhole, are known chemical reagents, and thus generate ions when in the presence of hydrocarbon molecules. In their presence, one can not consider the spectrum of a mixture as the superposition of individual spectra weighted by their respective concentration. The present disclosure introduces, instead, understanding and accounting for the newly generated molecules when calculating the respective compound concentrations.

The present disclosure thus introduces a method of analyzing a mass spectrometer signal in the presence of combined electron and chemical ionization of the sample under test. This method comprises the production of a tool response matrix, which together with a measurement of the sample pressure may be used to compute the component concentrations of interest in the sample under test.

Initially, obtaining the mass spectrum of a fluid comprises capturing a sample from a water- or oil-based mud stream on its return to the surface. Gases are then extracted from the sample and injected into the ionizing chamber of a mass spectrometer. The gas molecules are bombarded with high energy electrons, ejecting one electron from the molecules, and thus creating unstable ions which disintegrate. The resulting fragments may then be sent through a mass filter. FIG. 1 is a schematic view of a known 4-rod mass filter.

Referring to FIG. 1, DC and AC voltage are applied to filter the molecular ions and fragments traveling along the rods. Voltages are selected such that resonant ions are filtered according to their mass-to-charge values. The resulting spectrum indicates the abundance of a specific ion along with its mass (normalized by the charge on the ion).

Figure 2:
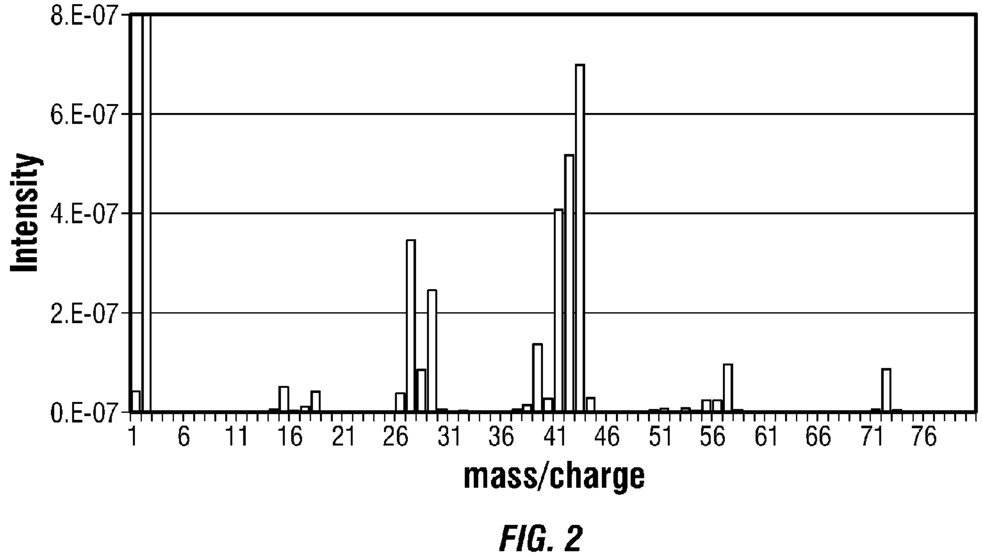
FIG. 2 is a graph demonstrating one or more aspects of the present disclosure.

One such spectrum, shown in FIG. 2, is typical of pentane molecules, having a molecular ion at mass 72 ($5^{12}C+12^{1}H$). The lower mass peaks correspond to the ions resulting from the partial fragmentation of the molecular ion—due to the fact that the molecular ion is an unpaired ion, making it very unstable. Isotopes (for example, $^{13}C$ instead of $^{12}C$) have their own peaks as a result of their mass; that is, molecular mass+1 for example for a pentane molecule with one $^{13}C$ and four $^{12}C$).

A typical spectrum has two major properties. First, the distribution in the spectrum is repeatable, unique (for a given electron energy), and is capable of being used to identify the sample. Second, the intensity is proportional to the sample concentration. In the absence of any effect other than electron ionization, the intensity of each peak from a mixture can be related to the concentration of the gas components by a linear mixing rule.

Figure 3A:
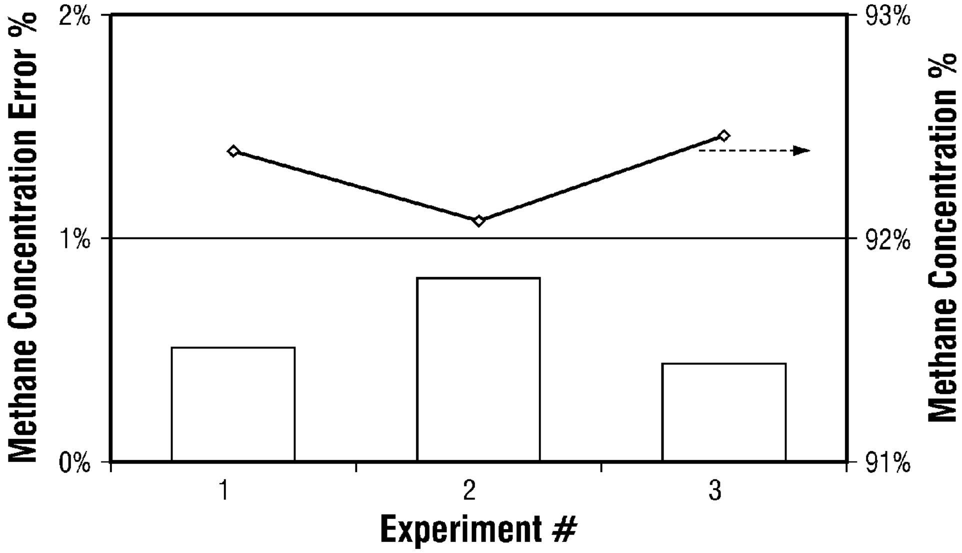
FIGS. 3A and 3B are graphs demonstrating one or more aspects of the present disclosure.
Figure 3B:
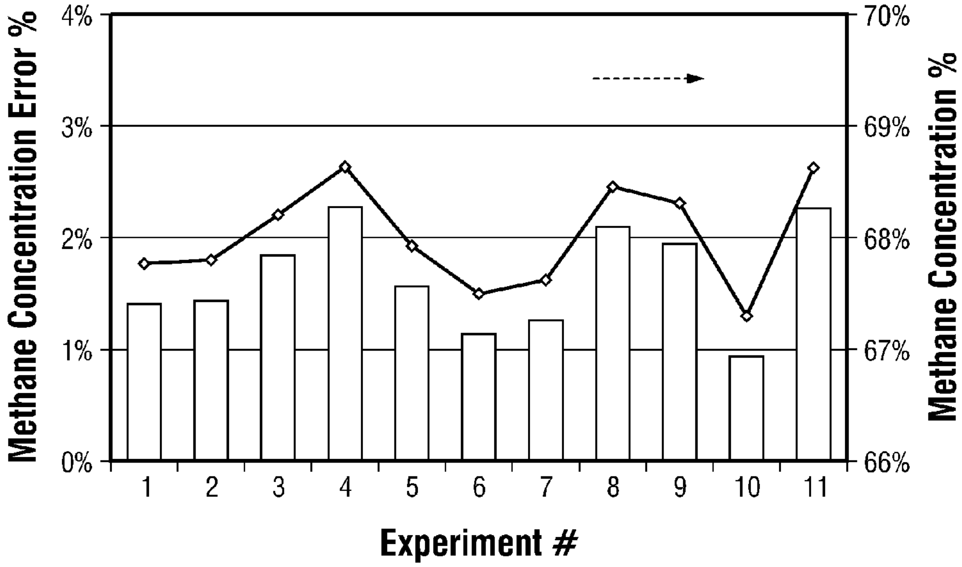

Consider two tests measuring concentrations of a mixture of pentane and hexane. The first test comprises three measurements of a mixture of 93% methane and 7% pentane. The results, shown in FIG. 3A, demonstrate a systematic error of 0.5% and a random error of less than 0.1% in the concentration (of methane). The second test comprises 11 measurements of a mixture of 67% methane and 33% pentane. The results, shown in FIG. 3B, demonstrate a repeatable measurement with a systematic error of 1.7% and a random error of less than 0.5%.

From such (or similar) experiments, the following equation can be formulated:

$$\begin{bmatrix} ^{1}a_5 & ^{1}a_6 \\ ^{2}a_5 & ^{2}a_6 \\ \cdots & \cdots \\ ^{73}a_5 & ^{73}a_6 \end{bmatrix} \times \begin{bmatrix} X_5 \cdot P \\ X_6 \cdot P \end{bmatrix} = \begin{bmatrix} ^{1}S \\ ^{2}S \\ \cdots \\ ^{73}S \end{bmatrix}$$

The first term is called the tool response matrix (TRM), the second term is called the concentration vector, and the third term is called the measured spectrum vector. The entries in the concentration vector consist of the product of the concentration (mole fraction) of each of the sample components and the sample pressure.

In the TRM, the value $^{j}a_i$ corresponds to the peak strength at mass j for the molecule i, and is equal to the value $^{j}S$ in the case of a single compound sample (molecule i). Each column of the tool response matrix is in fact the spectrum of an individual component in the compound. Once the spectrum [S] has been measured and the TRM is known, the concentrations of the individual sample components may be determined from the above matrix equation by well established methods. This is the case of electron impact ionization.

Chemical ionization, where one ion transfers its charge to a different molecule, is a source of complication. However, one or more aspects of the present disclosure may be utilized to successfully quantify its effect.

Figure 4:
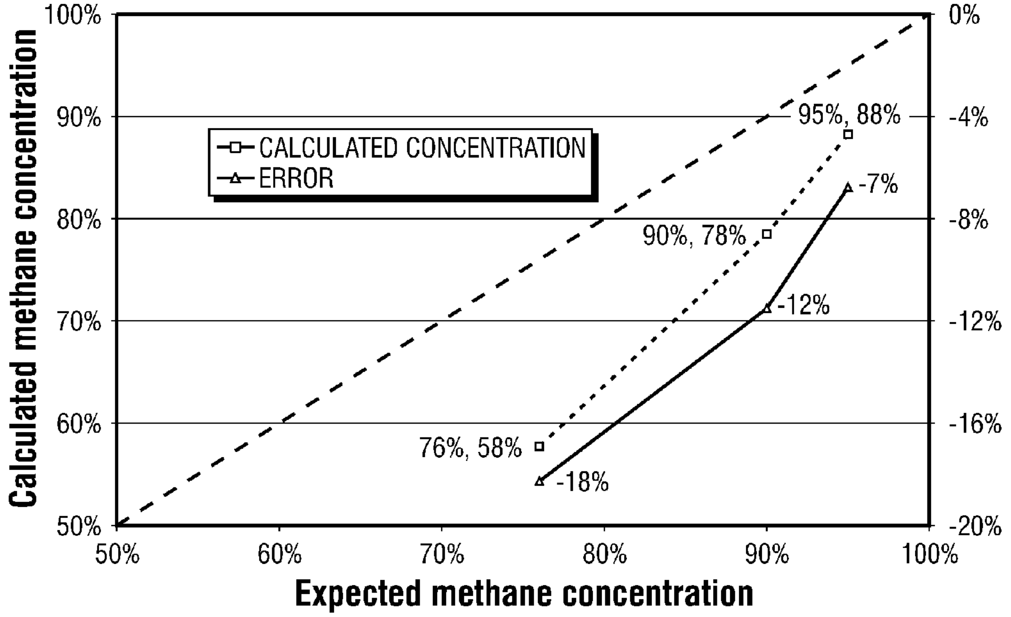
FIG. 4 is a graph demonstrating one or more aspects of the present disclosure.

Any molecular ion in a gas mixture causes chemical ionization of other species. The effect can be ignored for most hydrocarbons, except for methane and iso-butane. When applying the above-described matrix system (for the electron ionization process) to a mixture of methane and pentane, measurements for different concentrations show a larger than expected error, with lower than expected methane concentrations and higher than expected pentane concentrations. For example, as shown in FIG. 4, utilizing the above-described procedure applied to a mixture of 76% methane and 24% pentane may result in a measurement error as large as 12%.

However, it is known that methane is a chemical reagent that may be used to induce chemical ionization. Thus, for each single peak, the ratio of the signal S in mixture to the signal S in the pure compound is no longer $$\frac{^{y}S_{mixture}(CI)}{^{y}S_{pure}}$$

but instead becomes $$\frac{^{y}S_{mixture}(CI) + {}^{y}S_{mixture}(EI)}{^{y}S_{pure}}$$

with a new term generated by the chemical ionization effect.

Isotopes also provide evidence of the chemical ionization. The following table estimates the isotope contributions for various carbon groups.

TABLE 1

| Isotopic Contributions | |
|---|---|
| Isotopic Contribution | M + 1/M (%) |
| $C_1$ | 1.1 |
| $C_2$ | 2.2 |
| $C_3$ | 3.3 |
| $C_4$ | 4.4 |
| $C_5$ | 5.5 |
| $C_6$ | 6.6 |

For example, within a collection of one thousand carbon atoms, eleven $^{13}C$ will be present. For each 5-carbon atom, the chance to encounter a $^{13}C$ atom in the chain will be 5.5%. Thus, the chance to encounter two $^{13}C$ atoms in the same 5-carbon chain is so small that it may be disregarded.

In the ion abundance spectrum measured by the mass spectrometer, for a sample of methane ($CH_4$), the molecules are being bombarded by high energy electrons, which creates an unpaired ion $CH_4^+$. This ion has a mass of 16 g/mol for a carbon $^{12}C$ atom and a mass of 17 g/mol for a carbon $^{13}C$ atom.

Figure 5A:
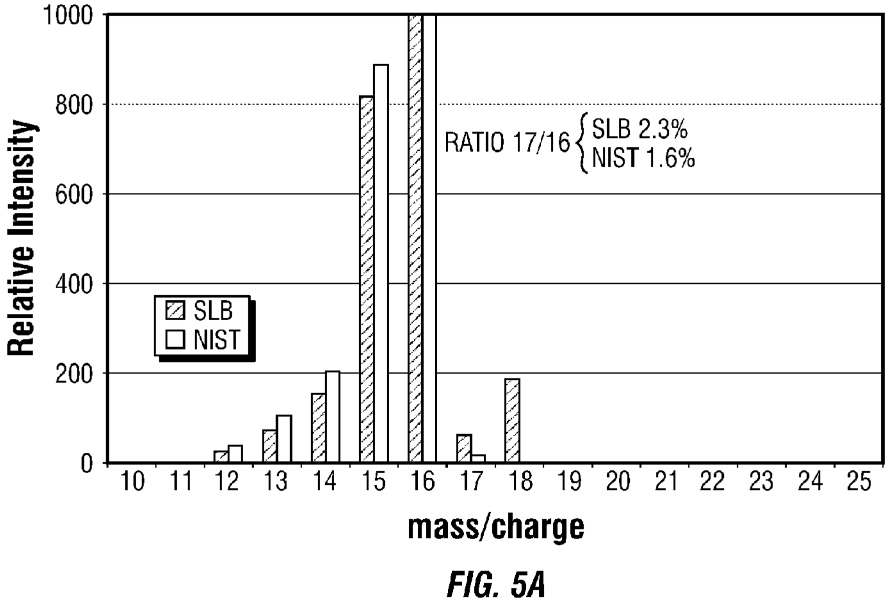
FIGS. 5A and 5B are graphs demonstrating one or more aspects of the present disclosure.
Figure 5B:
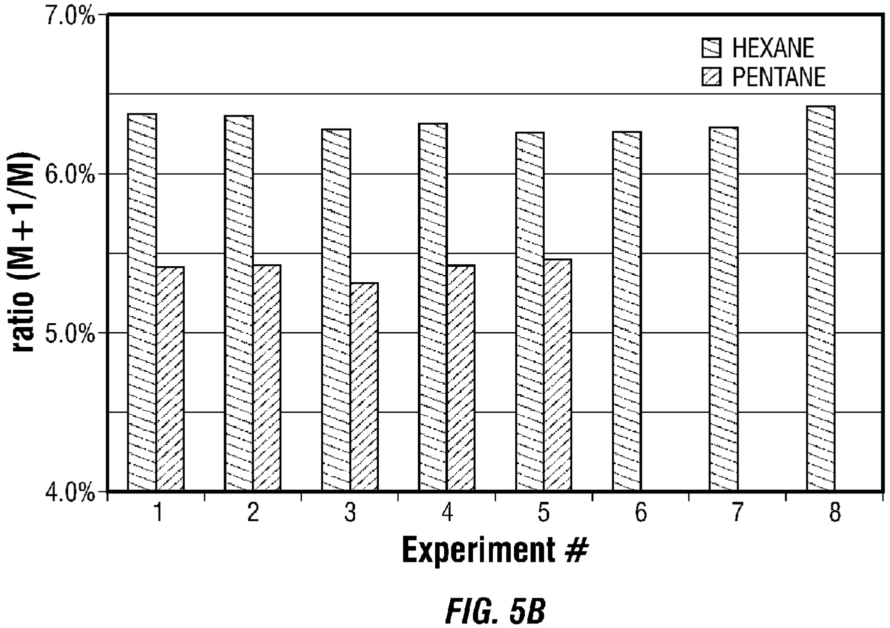

FIG. 5A is a graph showing the spectrum of pure methane obtained with a commercial mass spectrometer. By removing the contribution of water to the fragmentation pattern, the ratio of peak 17 over peak 16 is higher than expected, with a value of 2.3% instead of 1.1%. One conclusion which may be derived from this experiment is that ions, in particular, $CH_5^+$ are chemically generated. On the other hand, FIG. 5B is a graph showing results of measuring a spectrum of a sample of pentane and hexane, neither of which act as chemical reagents. The ratios of peak 73 over peak 72 and peak 87 over peak 86 are respectively 5.4% and 6.4%, which are very close to the values expected from considering the various isotopes (namely, 5.5% and 6.6%). It is concluded that, for this pair of chemicals, no substantial ions have been chemically generated.

The chemical ionization mechanism is briefly explained below to show the dependency of the newly generated ions to the sample total pressure and compound concentrations.

In a mixture of methane and pentane, for example, the electron ionization of methane $CH_4$ by high energy electrons creates an unstable unpaired ion $CH_4^+$:

$$CH_4+e^- \Longrightarrow CH_4^+.+2.e^- \rightarrow k_1=[CH_4^+.]/[CH_4] \quad (1)$$

This ion will react with the molecule of methane itself to create two different, very reactive ions:

$$CH_4^+.+CH_4 \Longrightarrow CH_5^++CH_3. \rightarrow k_2=[CH_5^+][CH_3.]/[CH_4^+.][CH_4] \quad (2)$$

$$CH_4^+.+CH_4 \Longrightarrow CH_3^++CH_5. \rightarrow k_3=[CH_3^+][CH_5.]/[CH_4^+.][CH_4] \quad (3)$$

These reactive ions ($CH_3^+$ and $CH_5^+$) react with the sample molecule ($C_5H_{12}$) to generate $C_5H_{13}^+$ (peak 73):

$$CH_4^+.+C_5H_{12} \Longrightarrow C_5H_{13}^++CH_3. \rightarrow k'_2=[C_5H_{13}^+][CH_3.]/[CH_4^+.][C_5H_{12}] \quad (4)$$

$$CH_5^++C_5H_{12} \Longrightarrow CH_4+C_5H_{13}^+ \rightarrow k_4=[CH_4][C_5H_{13}^+]/[CH_5^+][C_5H_{12}] \quad (5)$$

$$CH_3^++C_5H_{12} \Longrightarrow CH_2+C_5H_{13}^+ \rightarrow k_5=[CH_2][C_5H_{13}^+]/[CH_3^+][C_5H_{12}] \quad (6)$$

Concurrently, electron ionization of pentane, $C_5H_{12}$, results in:

$$C_5H_{12}+e^- \Longrightarrow C_5H_{12}^++2.e^- \rightarrow k_6=[C_5H_{12}^+]/[C_5H_{12}] \quad (7)$$

It is important to trace the factors affecting the number of ions generated by chemical ionization. To do so, the product equation path can be followed to isolate the concentration of $C_5H_{13}^+$. First, from above:

$$[CH_4]=X_1.P$$

$$[C_5H_{12}]=X_5.P$$

Then, from equation (1): $[CH_4^+.]=k_1.[CH_4]$.

Then, from equation (2): $[CH_5^+]=k_2.[CH_4^+.][CH_4]/[CH_3.]=k_2.[CH_4^+.].X_1/[CH_3.]$.

Then, from equation (5): $[C_5H_{13}^+]=k_4.[CH_5^+][C_5H_{12}]/[CH_4]=k_4.[CH_5^+.](X_5/X_1)$.

After substitution, the equation related to the $C_5H_{13}^+$ becomes:

$$[C_5H_{13}^+]=k_4.[CH_5^+][C_5H_{12}]/[CH_4]=k_1.k_2.k_4.(X_1.X_5).P^2/[CH_3.]$$

From equation (2), it can be seen that the peak $CH_3.$ varies linearly as a function of the sample pressure:

$$[CH_3.]=f(P)$$

As a conclusion, the effect of chemical ionization on peak 73 is dependent on pressure and mixture concentration:

$$[C_5H_{13}^+]=f(X_1.X_5,P)$$

To conclude this mechanism, chemically produced ions are dependent, for example in the interaction of methane and pentane, on the product of concentrations, $X_1.X_5$, and the sample pressure P.

For an n-gas mixture, the individual spectrum peak intensity ${}^yS$ is given by:

$${}^yS=\sum_{i=1}^{n} {}^ya_iX_iP+\sum_{j=1}^{n}\sum_{k=1}^{n}[({}^ya'_{j,k}X_jX_k+{}^yb'_{j,k})\cdot P+({}^ya'_{j,k}X_jX_k+{}^yb'_{j,k})]$$

In this model, the first term ${}^ya_iX_iP$ is as a result of electron ionization only and involves primary interactions. The second term describes binary molecular interactions (chemical ionization). Higher order interactions are less important and may be ignored. Once the model is established, and the peak intensities (S) in the mass spectrum are measured, the above expression (forward model or model) can be inverted to obtain the concentrations (X) of the mixture. The inversion (inversion model or model) process is well known in the art and may be an iterative process, for example, where an initial guess for the concentrations are used in the model to predict expected peak intensities which are then compared with the actually measured values. Based on the differences between the measured and calculated intensities, the concentrations are adjusted and the steps are repeated until the inversion converges and further variations in the concentrations fall below an acceptable tolerance. A processor may be used to perform these operations and may be located downhole or uphole.

It is clear from this discussion that the sample concentration may be measured without the need to separate the sample into its constituents (components). This is in contrast with other methods, such as gas chromatography, where the sample is first separated into individual components and each component is measured using different methods, including mass spectrometry.

The determination of the coefficients in the new coefficient matrix is done empirically through binary mixture experiments. For example, a binary mixture of methane and propane will provide the coefficients a', b', a", and b' related to chemical reaction between methane and propane. The same can be done for a binary mixture of methane and pentane and for any other pair of components present in the sample.

Figure 6A:
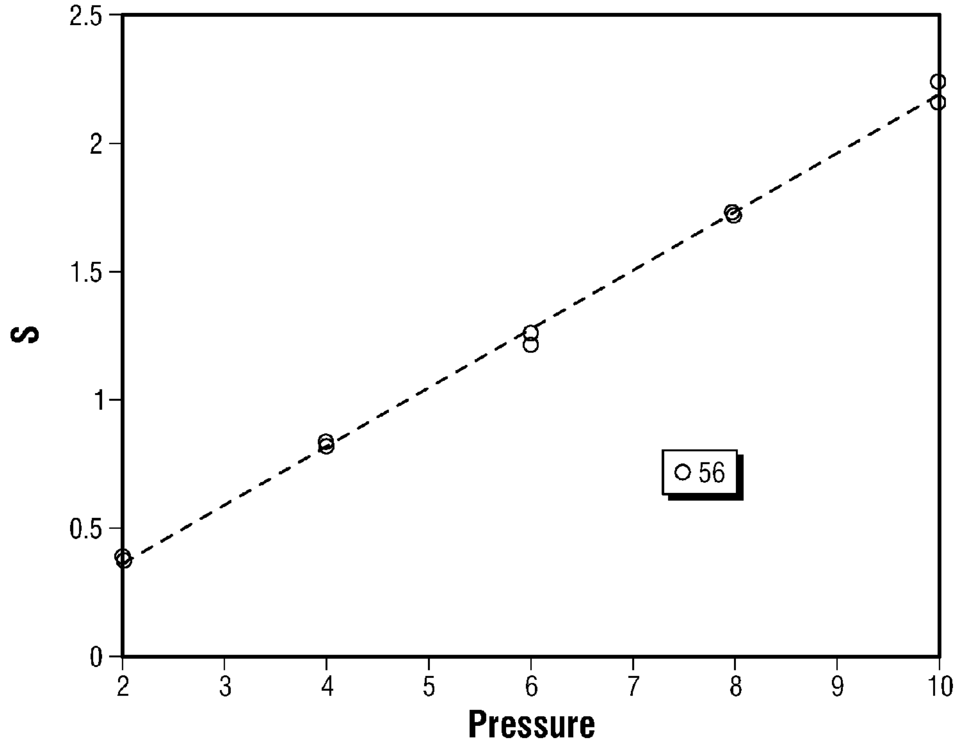
FIGS. 6A and 6B are graphs demonstrating one or more aspects of the present disclosure.
Figure 6B:
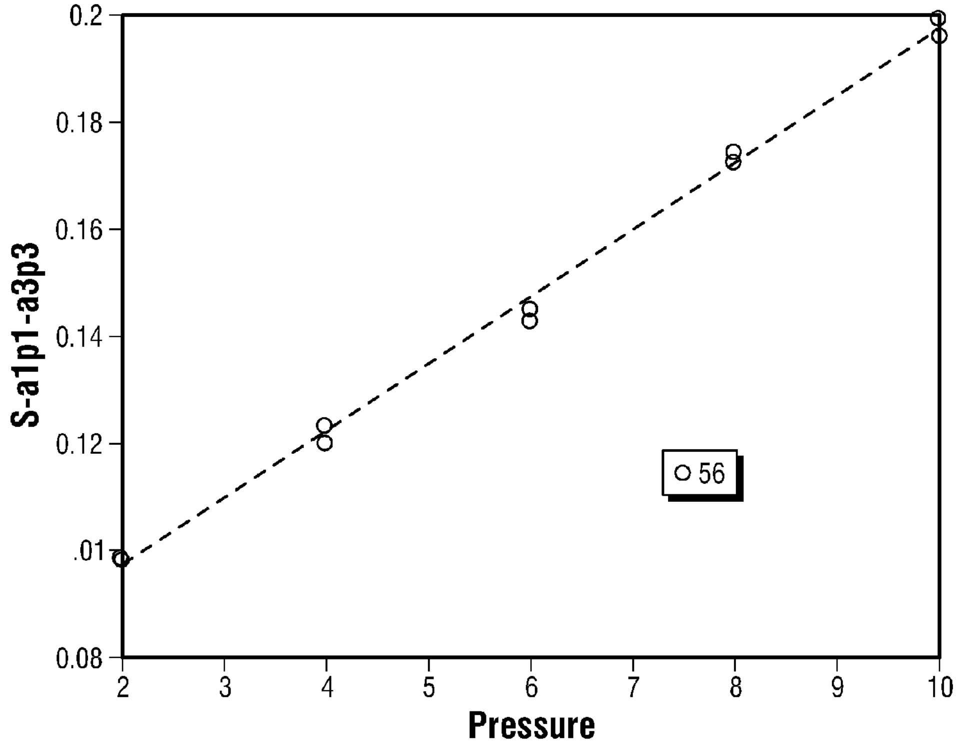

FIGS. 6A and 6B are graphs supporting the following description of obtaining the parameters. The measurements reflected in FIGS. 6A and 6B were performed with a mixture of methane and pentane at different pressures and concentrations. Pressure was varied between two and ten mtorr in 2 mtorr steps. Three mixtures were studied, including (1) 95% methane and 5% pentane, (2) 90% methane and 10% pentane, and (3) 76% methane and 24% pentane.

FIG. 6A shows the strength of the signal with the total pressure at the inlet of the mass spectrometer. If the first term (electron ionization model) is removed from the peak strength, FIG. 6B shows the result as still being a linear relationship with pressure and from which the slope and intercept for this peak at mass 56 can be determined as:

$$A={}^{56}a'_{1,5}X_1X_5+{}^{56}b'_{1,5}$$

$$B={}^{56}a''_{1,5}X_1X_5+{}^{56}b''_{1,5}$$

Figure 7A:
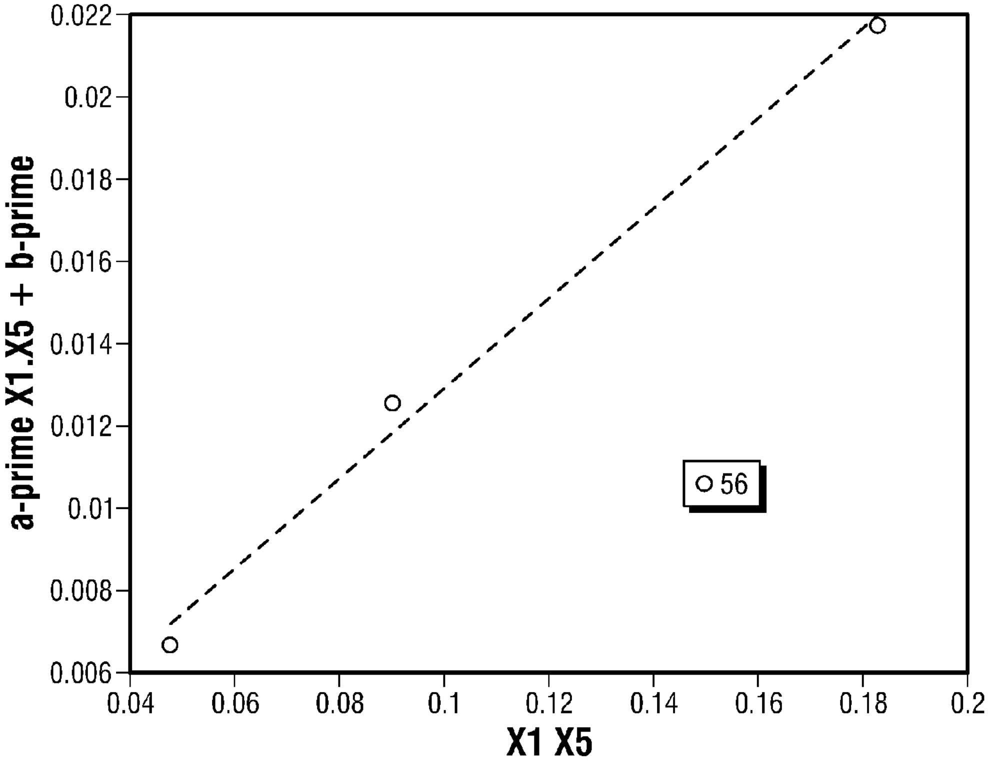
FIGS. 7A and 7B are graphs demonstrating one or more aspects of the present disclosure.
Figure 7B:
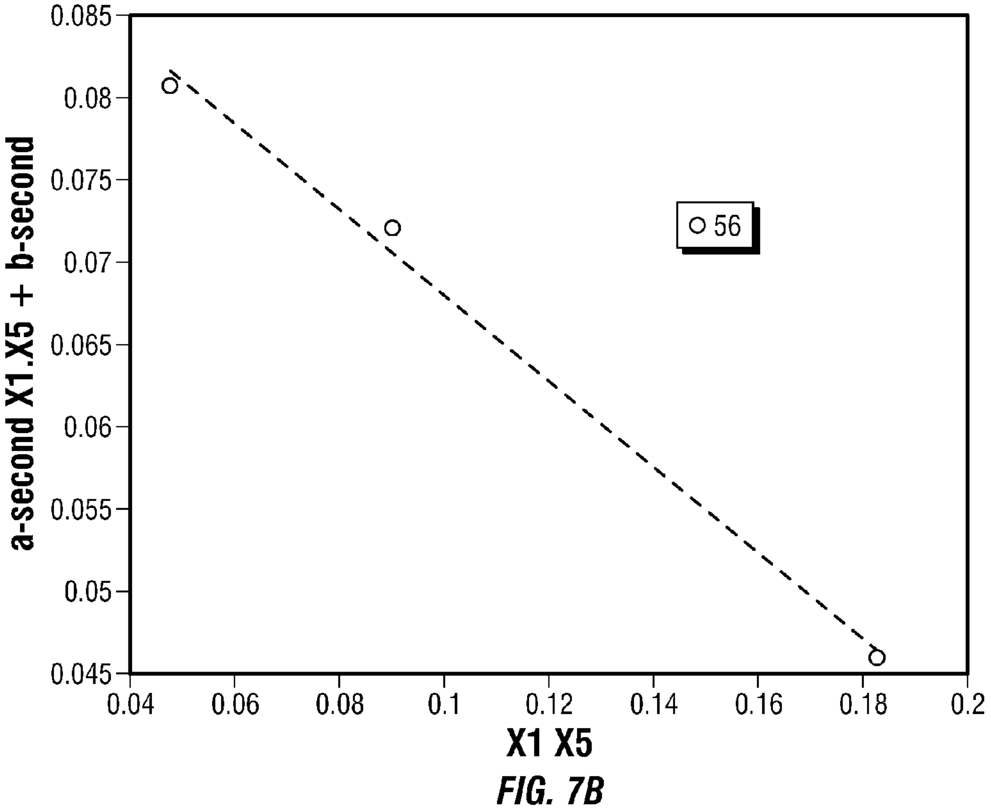

FIG. 7A is a graph plotting the values A (obtained for each mixture) as a function of the product of the component concentrations. From this, the slope and intersect can be calculated, thus obtaining the coefficients a' and b'. FIG. 7B is a graph plotting the values B (obtained for each mixture) as a function of the product of the component concentrations. From this, the slope and intersect can be calculated, thus obtaining the coefficients a" and b".

The same process can be performed for other peaks in the spectrum, which may be selected based on their relative strengths and mass location. For example, peak 44 would not be selected because of interferences from $CO_2$.

Figure 8A:
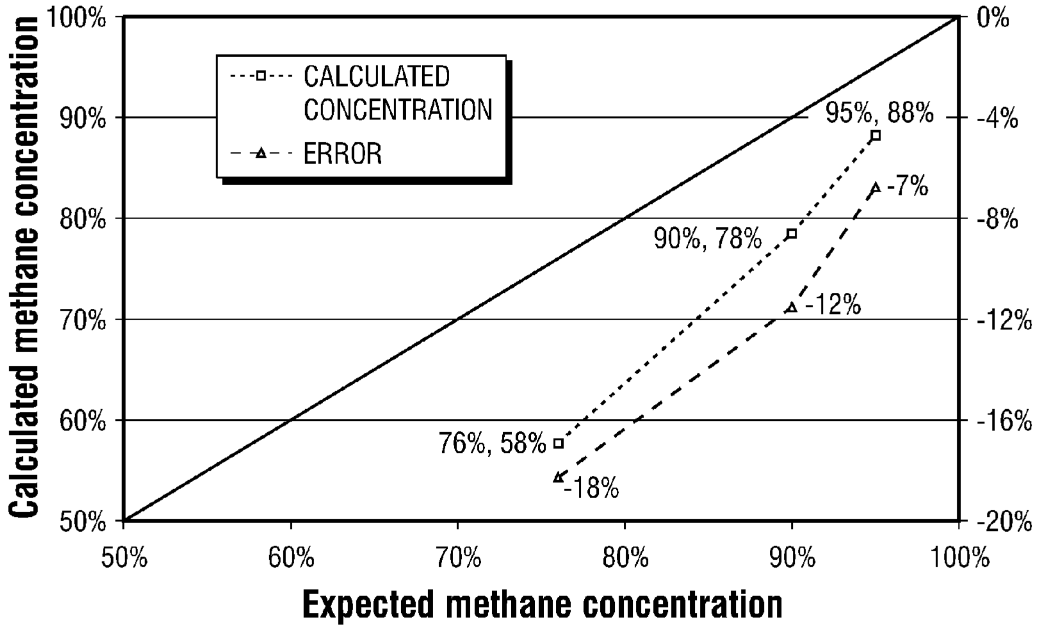
FIGS. 8A-8C are graphs demonstrating one or more aspects of the present disclosure.
Figure 8B:
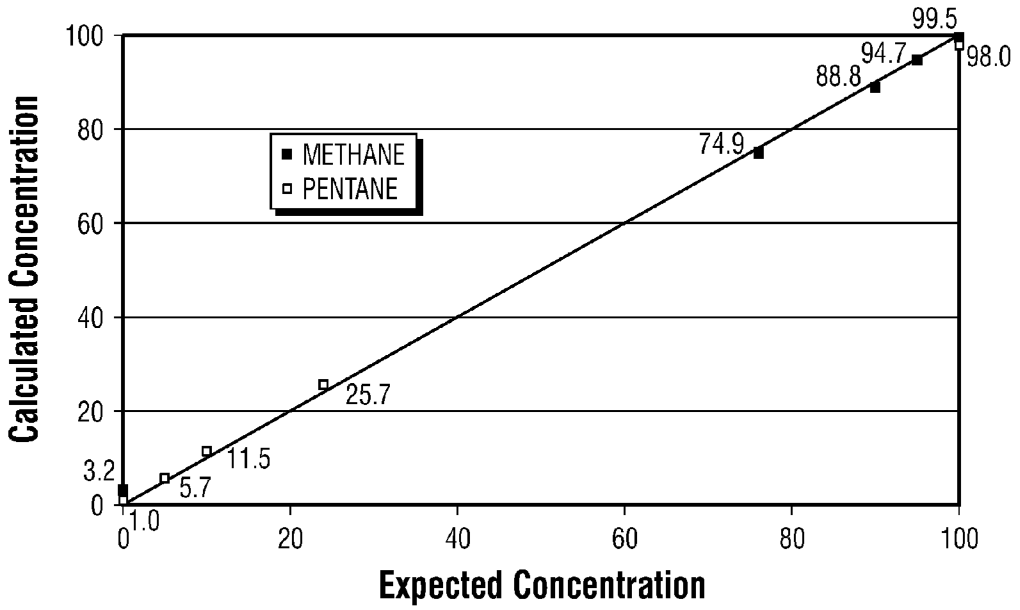

FIGS. 8A and 8B are graphs showing concentration measurements for different mixtures of methane and pentane, including (1) 100% methane, (2) 95% methane and 5% pentane, (3) 90% methane and 10% pentane, (4) 76% methane and 24% pentane, and (5) 100% pentane. FIG. 8A shows the results previously obtained with only the electron ionization model. FIG. 8B shows the results with the more complete model which combines the effects of electron and chemical ionization as introduced in the present disclosure. FIGS. 8A and 8B further demonstrate that errors resulting from utilizing the new model introduced herein may be within experimental and instrumentation errors.

Figure 8C:
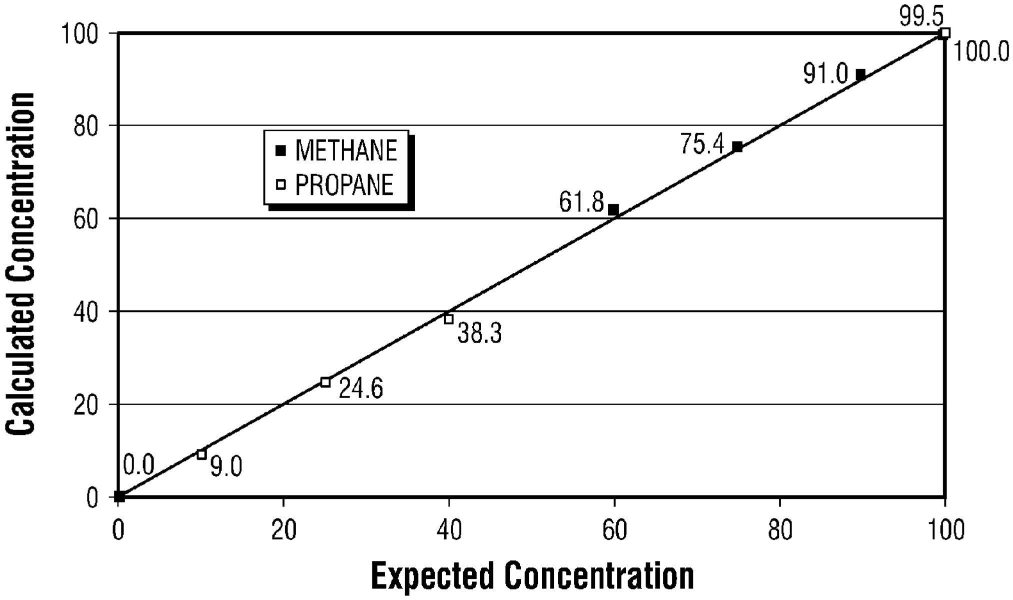

FIG. 8C is a graph showing similar results for concentration measurements for different mixtures of methane and propane, including (1) 100% methane, (2) 90% methane and 10% propane, (3) 75% methane and 25% propane, (4) 60% methane and 40% propane, and (5) 100% propane.

Figure 9A:
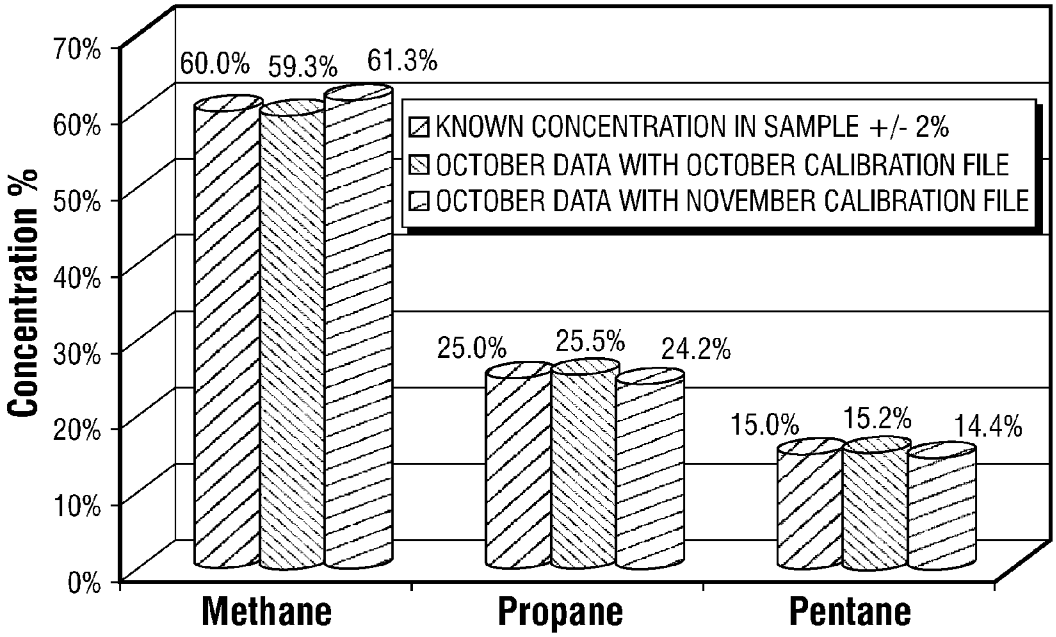
FIGS. 9A and 9B are graphs demonstrating one or more aspects of the present disclosure.
Figure 9B:
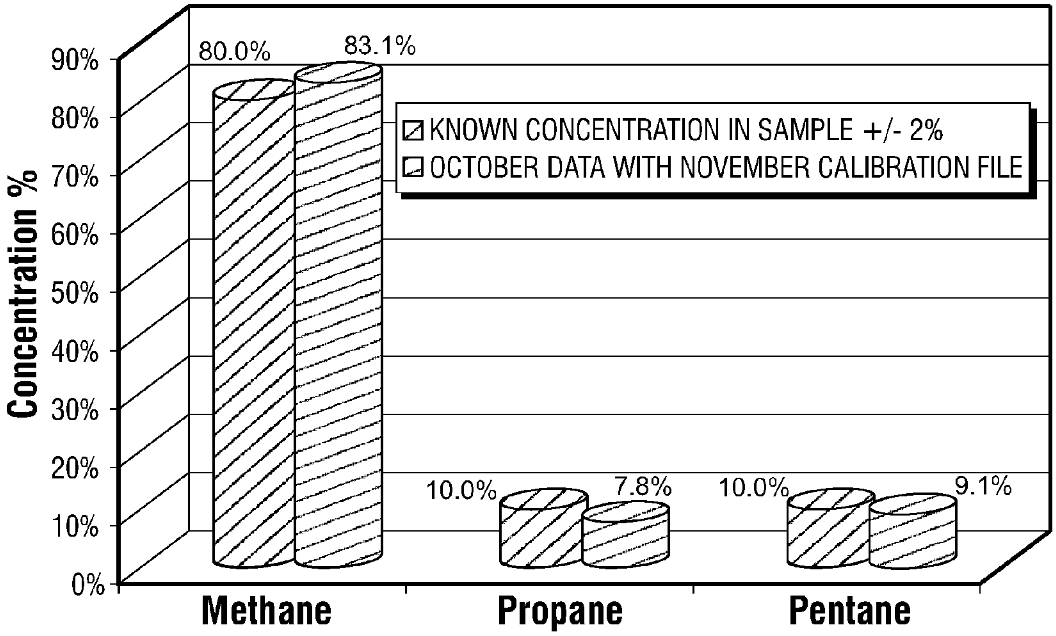

One or more of the aspects of the present disclosure may also be applicable to ternary mixtures. For example, aspects of the above-described electron and chemical ionization model may be utilized to determine concentrations of a ternary mixture. This is supported by experimental results with a methane, propane and pentane mixture. FIG. 9A presents such results for a mixture of 60% methane, 25% propane and 15% pentane, and FIG. 9B presents such results for a mixture of 80% methane, 10% propane and 10% pentane. To arrive at these results, a least-squares method was employed utilizing just six peak strengths and the combined electron and chemical ionization model described above. The results are shown in FIG. 9B. The derived component concentrations are within experimental and instrumentation errors.

The electron and chemical ionization model introduced herein may be particularly advantageous for mixtures having a methane content higher than 60%. This is within the expected concentrations of methane at locations around the globe, according to SPE 109861 "Advanced Mud Gas Logging in Combination With Wireline Formation Testing and Geochemical Fingerprinting for an Improved Understanding of Reservoir Architecture", which provides that different wells around the globe may have a high content of methane, as shown in the following table.

TABLE 2

Global Hydrocarbon Concentrations

| | Region | | | | | | | | |
|---|---|---|---|---|---|---|---|---|---|
| | Africa | | Gulf of Mexico | | | | | Middle East | |
| Component | HC | FLAIR | HC | FLAIR | Trad | HC | FLAIR | HC | FLAIR |
| C1 | 73.2 | 72.3 | 81.4 | 80.8 | 94.6 | 78.5 | 76.1 | 90.1 | 88.3 |
| C2 | 9.0 | 9.1 | 7.6 | 8.2 | 3.7 | 9.0 | 10.0 | 5.8 | 6.1 |
| C3 | 7.9 | 7.9 | 5.6 | 5.7 | 1.3 | 5.5 | 6.6 | 2.1 | 2.3 |
| i-C4 | 3.1 | 3.4 | 1.0 | 1.1 | 0.4 | 1.2 | 1.2 | 0.5 | 0.7 |
| n-C4 | 4.1 | 4.4 | 2.5 | 2.3 | 0.0 | 2.5 | 2.9 | 0.8 | 1.2 |
| i-C5 | 2.6 | 2.7 | 0.9 | 0.9 | 0.0 | 1.3 | 1.1 | 0.4 | 0.7 |
| n-C5 | 0.1 | 0.1 | 1.0 | 0.9 | 0.0 | 1.3 | 1.2 | 0.4 | 0.6 |
| WH | 26.8 | 27.6 | 18.6 | 19.1 | 5.4 | 20.9 | 23.2 | 10.0 | 11.6 |
| BH | 4.6 | 4.4 | 8.1 | 8.2 | 57.8 | 7.4 | 6.6 | 22.8 | 17.2 |

Figure 10A:
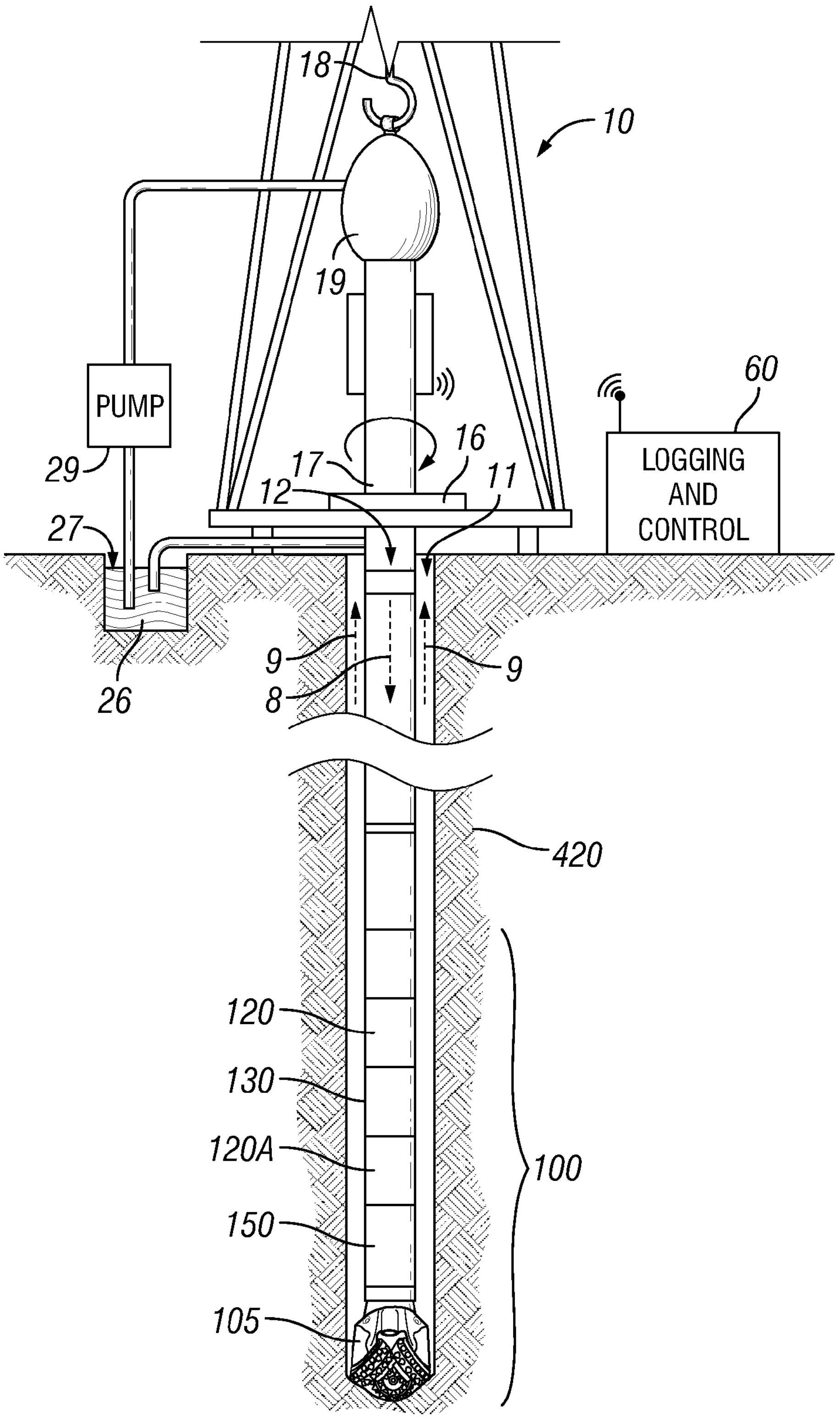
FIGS. 10A and 10B are schematic views of apparatus according to one or more aspects of the present disclosure.

Turning to FIG. 10A, an example well site system according to one or more aspects of the present disclosure is shown. The well site may be situated onshore (as shown) or offshore. The system may comprise one or more while-drilling devices 120, 120A, 130 that may be configured to be positioned in a wellbore 11 penetrating a subsurface formation 420. The wellbore 11 may be drilled through subsurface formations by rotary drilling in a manner that is well known in the art.

A drill string 12 may be suspended within the wellbore 11 and may include a bottom hole assembly (BHA) 100 proximate the lower end thereof. The BHA 100 may include a drill bit 105 at its lower end. It should be noted that in some implementations, the drill bit 105 may be omitted and the bottom hole assembly 100 may be conveyed via tubing or pipe. The surface portion of the well site system may include a platform and derrick assembly 10 positioned over the wellbore 11, the assembly 10 including a rotary table 16, a kelly 17, a hook 18 and a rotary swivel 19. The drill string 12 may be rotated by the rotary table 16, which is itself operated by well known means not shown in the drawing. The rotary table 16 may engage the kelly 17 at the upper end of the drill string 12. As is well known, a top drive system (not shown) could alternatively be used instead of the kelly 17 and rotary table 16 to rotate the drill string 12 from the surface. The drill string 12 may be suspended from the hook 18. The hook 18 may be attached to a traveling block (not shown) through the kelly 17 and the rotary swivel 19, which may permit rotation of the drill string 12 relative to the hook 18.

The surface system may include drilling fluid (or mud) 26 stored in a tank or pit 27 formed at the well site. A pump 29 may deliver the drilling fluid 26 to the interior of the drill string 12 via a port in the swivel 19, causing the drilling fluid 26 to flow downwardly through the drill string 12 as indicated by the directional arrow 8. The drilling fluid 26 may exit the drill string 12 via water courses, nozzles, or jets in the drill bit 05, and then may circulate upwardly through the annulus region between the outside of the drill string and the wall of the wellbore, as indicated by the directional arrows 9. The drilling fluid 26 may lubricate the drill bit 105 and may carry formation cuttings up to the surface, whereupon the drilling fluid 26 may be cleaned and returned to the pit 27 for recirculation.

The bottom hole assembly 100 may include a logging-while-drilling (LWD) module 120, a measuring-while-drilling (MWD) module 130, a rotary-steerable directional drilling system and hydraulically operated motor 150, and the drill bit 105. The LWD module 120 may be housed in a special type of drill collar, as is known in the art, and may contain a plurality of known and/or future-developed types of well logging instruments. It will also be understood that more than one LWD module may be employed, for example, as represented at 120A (references, throughout, to a module at the position of LWD module 120 may alternatively mean a module at the position of LWD module 120A as well). The LWD module 120 may include capabilities for measuring, processing, and storing information, as well as for communicating with the MWD 130. In particular, the LWD module 120 may include a processor configured to implement one or more aspects of the methods described herein. For example, the LWD module 120 may comprise a testing-while-drilling device configured to utilize the above-described electron and chemical ionization model to determine the composition of a fluid downhole, such as a borehole fluid, drilling fluid (mud), formation fluid sampled from the formation 420, and/or others.

The MWD module 130 may also be housed in a special type of drill collar, as is known in the art, and may contain one or more devices for measuring characteristics of the drill string and drill bit. The MWD module 130 may further include an apparatus (not shown) for generating electrical power for the downhole portion of the well site system. Such apparatus typically includes a turbine generator powered by the flow of the drilling fluid 26, it being understood that other power and/or battery systems may be used while remaining within the scope of the present disclosure. In the present example, the MWD module 130 may include one or more of the following types of measuring devices: a weight-on-bit measuring device, a torque measuring device, a vibration measuring device, a shock measuring device, a stick slip measuring device, a direction measuring device, and an inclination measuring device. Optionally, the MWD module 130 may further comprise an annular pressure sensor and/or a natural gamma ray sensor. The MWD module 130 may include capabilities for measuring, processing, and storing information, as well as for communicating with a logging and control unit 60. For example, the MWD module 130 and the logging and control unit 60 may communicate information (uplinks and/or downlinks) via mud pulse telemetry (MPT) and/or wired drill pipe (WDP) telemetry. In some cases, the logging and control unit 60 may include a controller having an interface configured to receive commands from a surface operator. Thus, commands may be sent to one or more components of the BHA 100, such as to the LWD module 120.

Figure 10B:
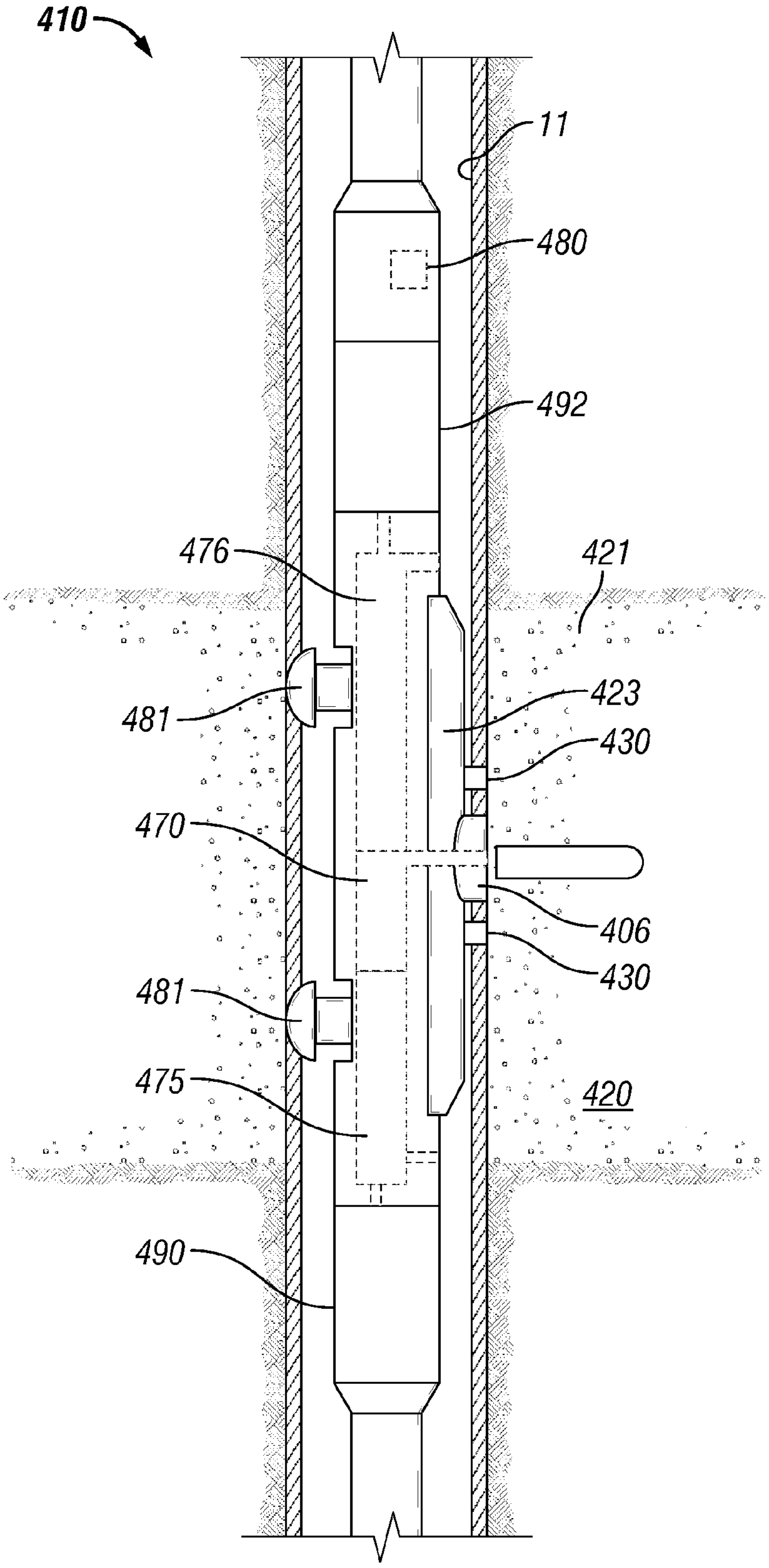

A testing-while-drilling device 410 (e.g., identical or similar to the LWD tool 120 in FIG. 10A) is shown in FIG. 10B. The testing-while-drilling device 410 may be provided with a stabilizer that may include one or more blades 423 configured to engage a wall of the wellbore 11. The testing-while-drilling device 410 may be provided with a plurality of backup pistons 481 configured to assist in applying a force to push and/or move the testing-while-drilling device 410 against the wall of the wellbore 411. The configuration of the blade 423 and/or the backup pistons 481 may be of a type described, for example, in U.S. Pat. No. 7,114,562, incorporated herein by reference. However, other types of blade or piston configurations may be used to implement the testing-while-drilling device 410 within the scope of the present disclosure. A probe assembly 406 may extend from the stabilizer blade 423 of the testing-while-drilling device 410. The probe assembly 406 may be configured to selectively seal off or isolate selected portions of the wall of the wellbore 411 to fluidly couple to an adjacent formation 420. Thus, the probe assembly 406 may be configured to fluidly couple components of the testing-while-drilling device 410, such as pumps 475 and/or 476, to the adjacent formation 420. Once the probe assembly 406 fluidly couples to the adjacent formation 420, various measurements may be conducted on the adjacent formation 420. For example, a pressure parameter may be measured by performing a pretest. Alternatively, or additionally, a sample may be withdraw from the formation 420 via the probe assembly 406, and this sample may be analyzed using the electron and chemical ionization model described above, possibly in conjunction with a spectrometer also position within the device 410 and/or other component of the drill string.

The pump 476 may be used to draw subterranean formation fluid 421 from the formation 420 into the testing-while-drilling device 410 via the probe assembly 406. The fluid may thereafter be expelled through a port into the wellbore, or it may be sent to one or more fluid analyzers disposed in a sample analysis module 492, which may receive the formation fluid for subsequent analysis. Such fluid analyzers may, for example, comprise a mass spectrometer and means for interpreting spectral data therefrom, such as to determine fluid composition utilizing the electron and chemical ionization model described above. The sample analysis module 492 may also or alternatively be configured to perform such analysis on fluid obtained from the wellbore and/or drill string. For example, the sample analysis module 492 may be configured for use in mud-gas logging operations, wherein gas extracted from mud before and/or after the bit is analyzed to determine composition and/or concentrations, as described above.

The stabilizer blade 423 of the testing-while-drilling device 410 may be provided with a plurality of sensors 430, 432 disposed adjacent to a port of the probe assembly 406. The sensors 430, 432 may be configured to determine petrophysical parameters (e.g., saturation levels) of a portion of the formation 420 proximate the probe assembly 406. For example, the sensors 430 and 432 may be configured to measure electric resistivity, dielectric constant, magnetic resonance relaxation time, nuclear radiation, and/or combinations thereof.

The testing-while-drilling device 410 may include a fluid sensing unit 470 through which the obtained fluid samples and/or injected fluids may flow, and which may be configured to measure properties of the flowing fluid. It should be appreciated that the fluid sensing unit 470 may include any combination of conventional and/or future-developed sensors within the scope of the present disclosure.

A downhole control system 480 may be configured to control the operations of the testing-while-drilling device 410. For example, the downhole control system 480 may be configured to control the extraction of fluid samples from the formation 420, wellbore and/or drill string, the analysis thereof, and any pumping thereof, for example, via the pumping rate of the pumps 475 and/or 476.

The downhole control system 480 may be further configured to analyze and/or process data obtained from the downhole sensors and/or disposed in the fluid sensing unit 470 or from the sensors 430, and/or the fluid analysis module 492. The downhole control system 480 may be further configured to store measurement and/or processed data, and/or communicate measurement and/or processed data to another component and/or the surface for subsequent analysis.

While the testing-while drilling device 410 is depicted with one probe assembly, multiple probes may be provided with the testing-while drilling device 410 within the scope of the present disclosure. For example, probes of different inlet sizes, shapes (e.g., elongated inlets) or counts, seal shapes or counts, may be provided.

Figure 11:
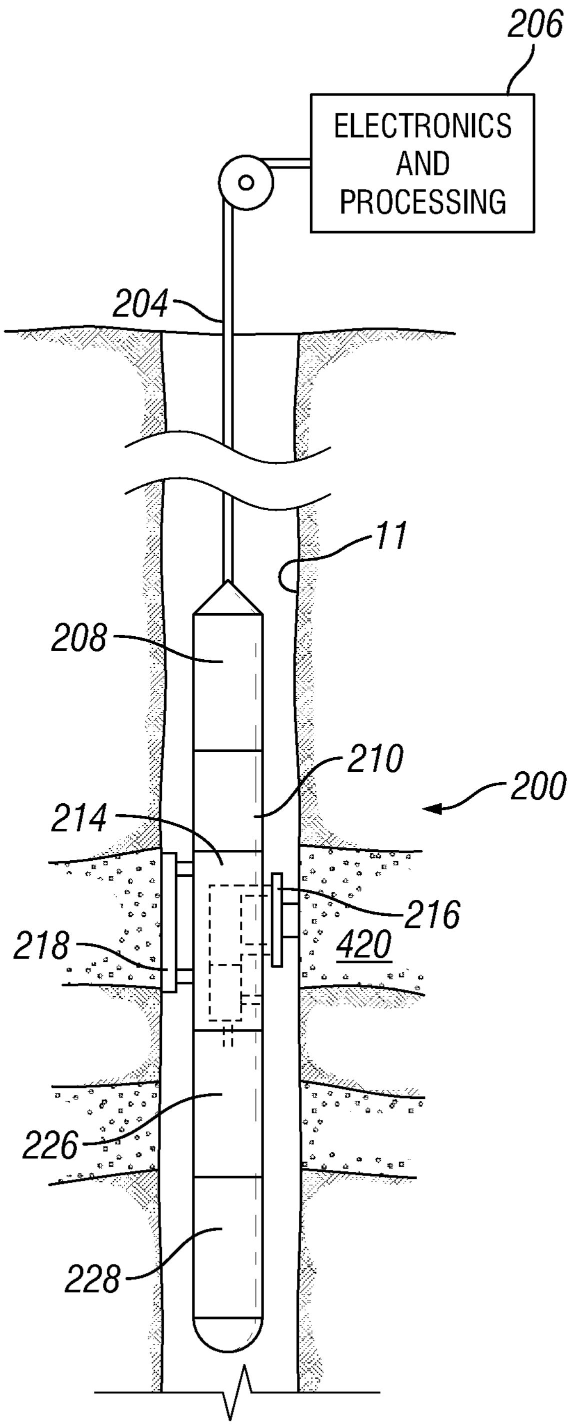
FIG. 11 is a schematic view of apparatus according to one or more aspects of the present disclosure.

Turning to FIG. 11, an example well site system according to one or more aspects of the present disclosure is shown. The well site may be situated onshore (as shown) or offshore. A wireline tool 200 may be configured to seal a portion of a wall of a wellbore 11 penetrating a subsurface formation 420.

The example wireline tool 200 may be suspended in the wellbore 11 from a lower end of a multi-conductor cable 204 that may be spooled on a winch (not shown) at the Earth's surface. At the surface, the cable 204 may be communicatively coupled to an electronics and processing system 206. The electronics and processing system 206 may include a controller having an interface configured to receive commands from a surface operator. In some cases, the electronics and processing system 206 may further include a processor configured to implement one or more aspects of the methods described herein.

The example wireline tool 200 may include a telemetry module 210, a formation tester 214, and other modules 226, 228. Although the telemetry module 210 is shown as being implemented separate from the formation tester 214, the telemetry module 210 may be implemented in the formation tester 214. Additional components may also be included in the tool 200.

The formation tester 214 may comprise a selectively extendable probe assembly 216 and a selectively extendable tool anchoring member 218 that are respectively arranged on opposite sides of the body 208. The probe assembly 216 may be configured to selectively seal off or isolate selected portions of the wall of the wellbore 11. Thus, the probe assembly 216 may be configured to fluidly couple pumps and/or other components of the formation tester 214 to the adjacent formation 420.

The formation tester 214 may be used to obtain fluid samples from the formation 420. A fluid sample may thereafter be expelled through a port into the wellbore or the sample may be sent to one or more fluid collecting or analyzing chambers disposed in the one or more other modules 226, 228. The above-described analysis may then be performed on the formation fluid.

The probe assembly 216 of the formation tester 214 may be provided with a plurality of sensors 222 and 224 disposed adjacent to a port of the probe assembly 216. The sensors 222 and 224 may be configured to determine petrophysical parameters (e.g., saturation levels) of a portion of the formation 420 proximate the probe assembly 216. For example, the sensors 222 and 224 may be configured to measure or detect one or more of electric resistivity, dielectric constant, magnetic resonance relaxation time, nuclear radiation, and/or combinations thereof.

The formation tester 214 may be provided with an additional fluid sensing unit (not shown) through which the obtained fluid samples and/or injected fluids may flow and which is configured to measure properties and/or composition data of the flowing fluids. For example, the fluid sensing unit may include a fluorescence sensor, such as described in U.S. Pat. Nos. 7,002,142 and 7,075,063, incorporated herein by reference. The fluid sensing unit may alternatively or additionally include an optical fluid analyzer, for example as described in U.S. Pat. No. 7,379,180, incorporated herein by reference. The fluid sensing unit may alternatively or additionally comprise a density and/or viscosity sensor, for example as described in U.S. Patent Application Pub. No. 2008/0257036, incorporated herein by reference. The fluid sensing unit may alternatively or additionally include a high resolution pressure and/or temperature gauge, for example as described in U.S. Pat. Nos. 4,547,691 and 5,394,345, incorporated herein by reference. An implementation example of sensors in the fluid sensing unit may be found in "New Downhole-Fluid Analysis-Tool for Improved Formation Characterization" by C. Dong, et al., SPE 108566, December 2008. It should be appreciated, however, that the fluid sensing unit may include any combination of conventional and/or future-developed sensors within the scope of the present disclosure.

The telemetry module 210 may comprise a downhole control system communicatively coupled to the electrical control and data acquisition system 206. The electrical control and data acquisition system 206 and/or the downhole control system may be configured to control the probe assembly 216, the extraction of fluid samples from the formation 230, and/or extraction of fluid from the drill string or borehole. The electrical control and data acquisition system 206 and/or the downhole control system may be further configured to analyze and/or process data obtained from downhole sensors, store measurements or processed data, and/or communicate measurements or processed data to the surface or another component for subsequent analysis.

Figure 12:
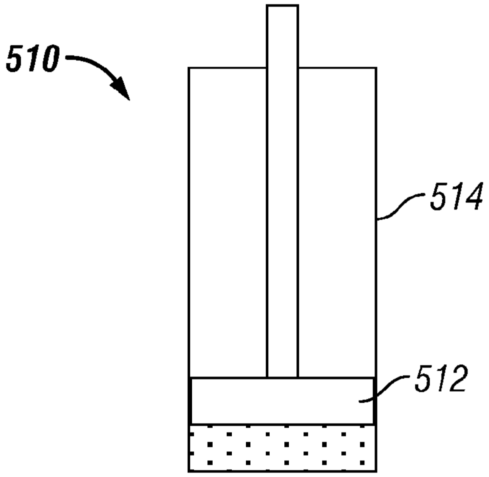
FIG. 12 is a schematic view of apparatus according to one or more aspects of the present disclosure.

In any of the implementations described above or otherwise within the scope of the present disclosure, liquid samples to be analyzed may be obtained from the formation, from drilling mud travelling down the drill string (for "before the bit" measurements), and/or from drilling mud in the annulus between the drill string and the wellbore wall (for "after the bit" measurements). Such samples may comprise at least one of hydrocarbons, hydrogen sulfide, carbon dioxide, nitrogen, hydrogen and helium. Such samples may be expanded by using a cylinder and piston, or by fixed volume chambers. A cylinder/piston arrangement 510 as schematically shown in FIG. 12 may be employed to expand the volume incrementally from zero up to a maximum volume. At each incremental volume, a portion of the initial pressurized fluid transforms to gas and exerts a pressure on the piston 512. As a result, the liquid volume reduces. This or a similar cylinder/piston arrangement may be implemented in one or more of the modules shown in FIGS. 10A, 10B and/or 11 to prepare samples for subsequent analysis that utilizes the chemical and electron ionization model described above.

Figure 13:
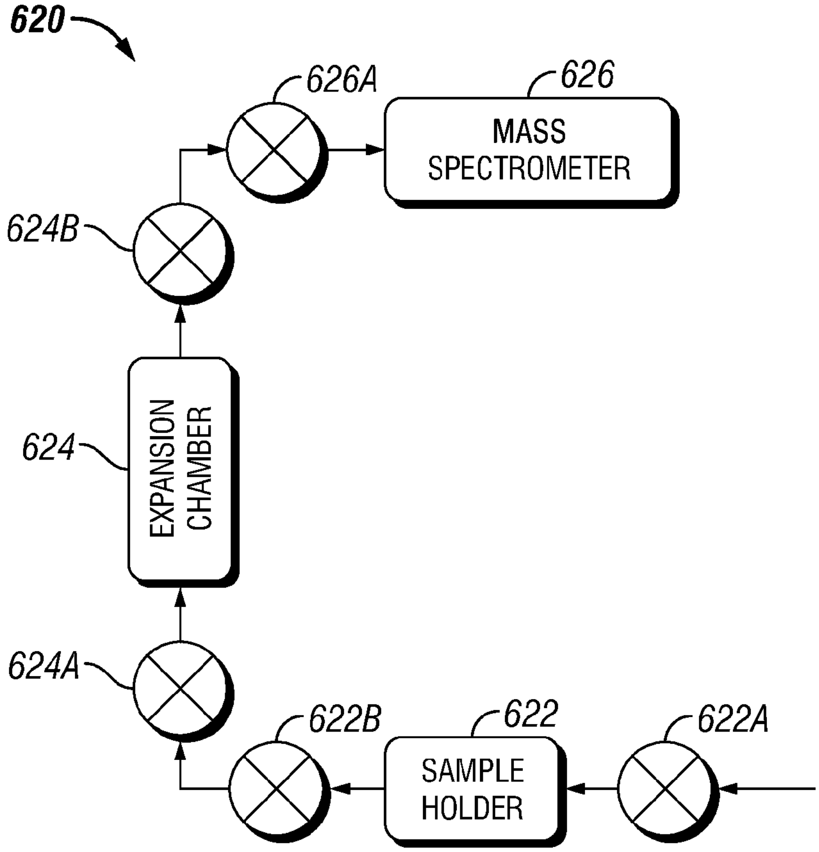
FIG. 13 is a schematic view of apparatus according to one or more aspects of the present disclosure.

Fixed volume chamber expansion is another method which may be employed. FIG. 13 is a schematic view of an example of such apparatus 620 which may be employed to expand a liquid sample into a fixed volume. The process of filling the sample holder 622 may be configured such that the entire volume of the sample holder 622 is filled with liquid (e.g., formation fluid, pre-bit drilling mud, and/or post-bit drilling mud). As such, the volume of the sample may be accurately known from a single calibration of the volume of the sample holder 622. This filling can be performed, for example, by flowing sample through the sample holder 622 via operation of an input valve 622*a* and an output valve 622*b*. Closing these two valves 622*a* and 622*b* may therefore trap a known volume of sample.

As shown in FIG. 13, an expansion chamber 624 is connected to the sample holder 622 through an input valve 624*a*. While the input valve 624*a* is closed, the chamber 624 is evacuated. Expansion takes place when an output valve 624*b* is closed and input valve 624*a* is opened, thereby connecting the liquid sample in the sample holder 622 to the empty volume of the expansion chamber 624. As with cylinder/piston embodiment described above, some components in the liquid expand and fill the expansion chamber 624, reducing the volume and changing the composition of liquid. Since the volume of the expansion chamber 624 is fixed, the volatile components in the sample fill the chamber 624. This gas may then be allowed to enter the mass spectrometer 626 for analysis that utilizes the above-described chemical and electron ionization model. The mass spectrometer 626 may be or comprise a quadrupole mass spectrometer, a time-of-flight mass spectrometer, and/or an ion trap mass spectrometer, among others.

Figure 14:
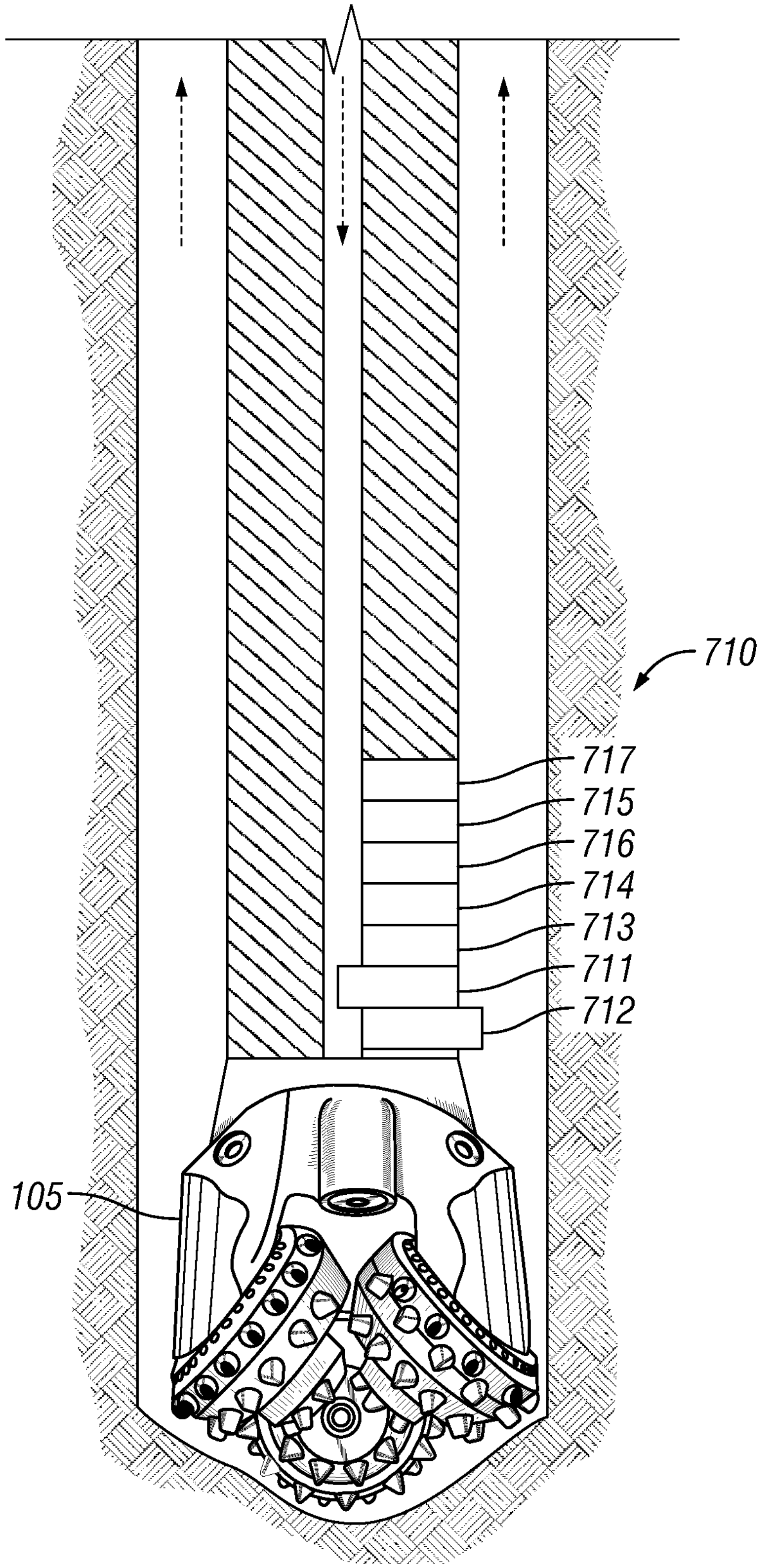
FIG. 14 is a schematic view of apparatus according to one or more aspects of the present disclosure.

Techniques described herein can be performed using various types of downhole equipment. FIG. 14 shows a diagram of a subsystem 710 according to one or more aspects of the present disclosure. The subsystem 710 may, for example, be at least a portion of one of the modules shown in FIGS. 10A and/or 10B, among others within the scope of the present disclosure. The modules of subsystem 710 may be configured to communicate with each other. The subsystem 710 includes sampling modules 711 and 712. The module 711 samples the mud within the drill collar before it reaches the drill bit 105 to obtain a pre-bit sample, and the module 712 samples the mud, including entrained components, in the annulus after passage through the drill bit 105 to obtain a post-bit sample. It will be understood that the sampling modules 711 and 712 may share at least some components. The subsystem 710 also includes separating and analyzing modules 713 and 714, respectively, and an electronic processor 715, which has associated memory (not separately shown), sample storage and disposition module 716, which can store selected samples and can also expel samples and/or residue to the annulus, and local communication module 717 configured to communicate with one or more other communications components within the drill string. It will be understood that some of the individual modules may be in plural form.

Figure 15:
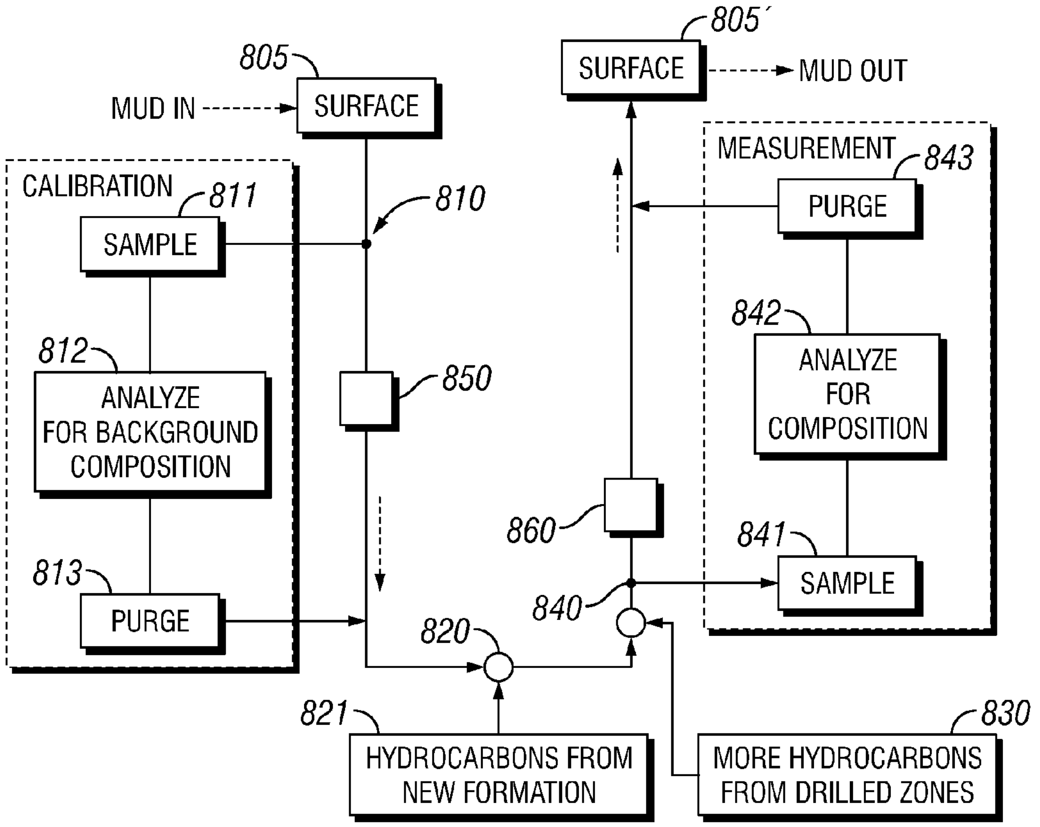
FIG. 15 is a schematic view of apparatus according to one or more aspects of the present disclosure.

FIG. 15 is a diagram that illustrates a process according to one or more aspects of the present disclosure which may utilize above-described techniques. Drilling mud from a surface location 805 arrives, after travel through the drill string, at a (pre-bit) calibration measurement location 810, where sampling (block 811), analysis for background composition 812, and purging (block 813) may be implemented. The mud then passes the drill bit 820, and hydrocarbons (as well as other fluids and solids) from a new formation being drilled into (block 821) are mixed with the mud. The mud in the annulus will also contain hydrocarbon and other components from zones already drilled through (block 830). The mud in the annulus arrives at (post-bit) measurement location 840, where sampling (block 841), analysis for composition (block 842) and purging (block 843) may be implemented, and the mud in the annulus then returns toward the surface (805'). The processor 715 (FIG. 14) may be configured to determine component concentrations utilizing the above-described combined chemical and electron ionization model.

Figure 16:
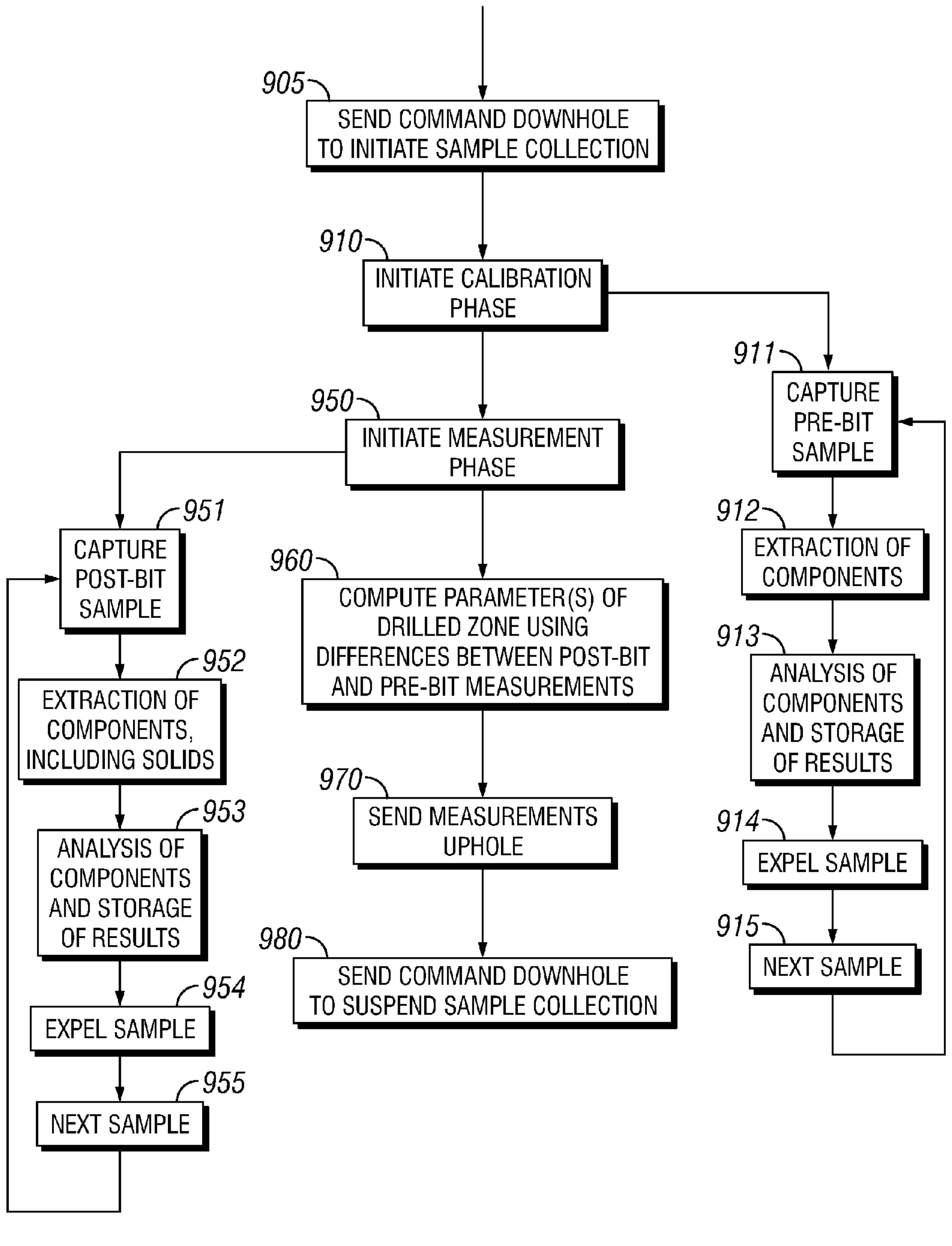
FIG. 16 is a flow-chart diagram of at least a portion of a method according to one or more aspects of the present disclosure.

FIG. 16 is a flow diagram of an example routine for controlling the uphole and downhole processors in implementing one or more aspects of the present disclosure. The block 905 represents sending of a command downhole to initiate collection of samples at preselected times and/or depths. A calibration phase is then initiated (block 910), and a measurement phase is also initiated (block 950). The calibration phase includes blocks 910-915.

The block 911 represents capture (by module 711 of FIG. 14) of a sample within the mud flow in the drill collar before it reaches the drill bit. Certain components are extracted from the mud (block 912), and analysis is performed on the pre-bit sample using, for example, the analysis module(s) 713 of FIG. 14, as well as storage of the results as a function of time and/or depth (block 913). The block 914 represents expelling of the sample (although here, as elsewhere, it will be understood that some samples, or constituents thereof, may be retained). Then, if this part of the routine has not been terminated, the next sample (block 915) is processed, beginning with re-entry to block 911.

The measurement phase, post-bit, includes blocks 951-955. The block 951 represents capture (by module 712 of FIG. 14) of a post-bit sample within the annulus, which will include entrained components, matrix rock and fluids, from the drilled zone. The block 952 represents extraction of components, including solids and fluids, and analysis is performed using, for example, the analysis module(s) 713 of FIG. 14, as well as storage of the results as a function of time and/or depth (block 953). The sample can then be expelled (block 954). (Again, if desired, some samples, or constituents thereof, can be retained.) Then, if this part of the routine has not been terminated (e.g., by command from uphole and/or after a predetermined number of samples, an indication based on a certain analysis result, etc.), the next sample (block 955) is processed, beginning with re-entry to block 951.

The block 960 represents optional computation of parameter(s) of the drilled zone using comparisons between the post-bit and pre-bit measurements. The block 970 represents the transmission of measurements uphole. These can be the analysis measurements, computed parameters, and/or any portion or combination thereof. Uphole, the essentially "real time" measurements can, optionally, be compared with surface mud logging measurements or other measurements or data bases of known rock and fluid properties (e.g., fluid composition or mass spectra). The block 980 represents the transmission of a command downhole to suspend sample collection until the next collection phase.

Regarding the command to the downhole tool to initiate sampling and analysis, the decision as to when to take a sample, or the frequency of sampling, can be based on various criteria. An example of one such criterion being to downlink to the tool every time a sample is required. Another example being to take a sample based on the reading of some open hole logs, e.g., resistivity, NMR, and/or nuclear logs. Yet another example being to take a sample based on a regular increment or prescribed pattern of measured depths or time.

After the sample is captured, a first extraction step comprises extracting, from the sample, gases which are present, and volatile hydrocarbon components as a gas. When extraction is performed at the surface, a first step may comprise dropping the pressure in the mud return line and flashing the gas into a receptacle, as described above. To improve the extraction of gases, agitators of various forms may be used. For volatile, and not so volatile liquids, steam stills may be employed. To expand the volume of a mud sample captured within a down hole tool, a cylinder and piston device can be used, as described above. Other methods may also or alternatively be used, including the use of a reversible down hole pump, or gas selective membranes, one for each gas. Alternatively, the liquid sample can be passed through a nozzle into a second chamber of lower pressure, which may ensure that the gas from all the liquid volume has been extracted and does not rely on stirring the sample. A simple pressure reduction can work well for small volume samples, but when the sample volume is large the sample may require stirring. Other types of mechanical separation such as centrifuging, can also be used. For example, once the volatiles have been extracted, they can be passed through moisture absorbing column, commonly known as desiccant, and then forwarded to the gas separation and measurement system, such as FTIR and/or quadrupole MS.

After hydrocarbons and other gases have been extracted, the above-described compositional analysis can be performed.

Figure 17:
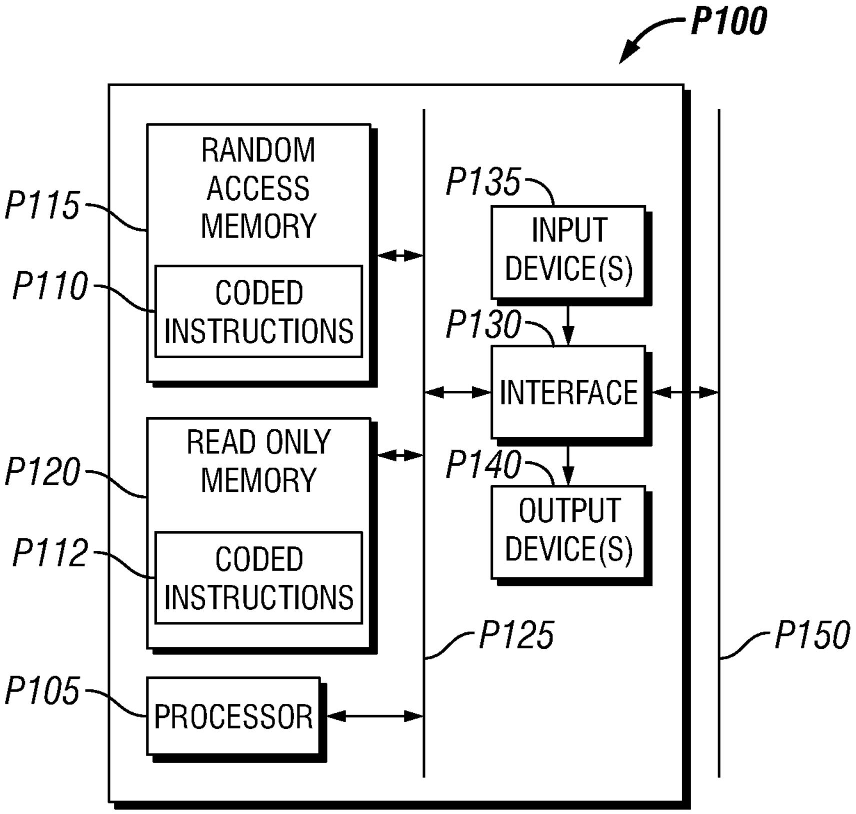
FIG. 17 is a schematic view of apparatus according to one or more aspects of the present disclosure.

FIG. 17 is a schematic view of at least a portion of an example computing system P100 that may be programmed to carry out all or a portion of the above-described methods of analysis and/or other methods within the scope of the present disclosure. The computing system P100 may be used to implement all or a portion of the electronics, processing and/or control systems and/or components described above, and/or other control means within the scope of the present disclosure. The computing system P100 shown in FIG. 17 may be used to implement surface components (e.g., components located at the Earth's surface) and/or downhole components (e.g., components located in a downhole tool) of a distributed computing system.

The computing system P100 may include at least one general-purpose programmable processor P105. The processor P105 may be any type of processing unit, such as a processor core, a processor, a microcontroller, etc. The processor P105 may execute coded instructions P110 and/or P112 present in main memory of the processor P105 (e.g., within a RAM P115 and/or a ROM P120). When executed, the coded instructions P110 and/or P112 may cause the formation tester or the testing while drilling device to perform at least a portion of the above-described methods, among other operations.

The processor P105 may be in communication with the main memory (including a ROM P120 and/or the RAM P115) via a bus P125. The RAM P115 may be implemented by dynamic random-access memory (DRAM), synchronous dynamic random-access memory (SDRAM), and/or any other type of RAM device, and ROM may be implemented by flash memory and/or any other desired type of memory device. Access to the memory P115 and the memory P120 may be controlled by a memory controller (not shown). The memory P115, P120 may be used to store, for example, measured formation properties (e.g., formation resistivity), petrophysical parameters (e.g., saturation levels, wettability), injection volumes and/or pressures.

The computing system P100 also includes an interface circuit P130. The interface circuit P130 may be implemented by any type of interface standard, such as an external memory interface, serial port, general-purpose input/output, etc. One or more input devices P135 and one or more output devices P140 are connected to the interface circuit P130. The example input device P135 may be used to, for example, collect data from the above-described sensors and/or analyzing devices. The example output device P140 may be used to, for example, display, print and/or store on a removable storage media one or more of measured formation properties (e.g., formation resistivity values or images), petrophysical parameters (e.g., saturation levels or images, wettability), injection volumes and/or pressures. Further, the interface circuit P130 may be connected to a telemetry system P150, including, a multi-conductor cable, mud pulse telemetry (MPT) and/or wired drill pipe (WDP) telemetry. The telemetry system P150 may be used to transmit measurement data, processed data and/or instructions, among other things, between the surface and downhole components of the distributed computing system.

In view of all of the above, the present disclosure introduces a method comprising: obtaining a mass spectrum of a sample; and determining a concentration of a component of the composition of the sample by utilizing a model of chemical and electron ionization and the obtained mass spectrum. The composition may be at least one of: formation fluid sampled from a subterranean formation, drilling mud sampled from within a drill string, and drilling mud sampled from an annulus formed between the drill string and a borehole penetrating the subterranean formation. Obtaining the mass spectrum may be performed downhole. Determining the concentration of the component may be performed downhole. Determining the concentration of the component may comprise determining a proportion of the component relative to another component of the composition. The chemical and electron ionization model may be linear in pressure. The chemical and electron ionization model may be calibrated for primary and binary interactions of the component. The chemical and electron ionization model may not be calibrated for tertiary or higher interactions of the component. The sample may have an unknown composition prior to performing the method. The method may further comprise determining a concentration of another component of the composition of the sample by again utilizing the chemical and electron ionization model and the obtained mass spectrum. Determining the concentrations of the components may comprise determining a relative concentration of the components. The method may not utilize gas chromatography.

The present disclosure also introduces an apparatus, comprising: means for obtaining a mass spectrum of a sample; and means for determining a concentration of a component of the composition of the sample by utilizing a model of chemical and electron ionization and the obtained mass spectrum. The composition may be at least one of: formation fluid sampled from a subterranean formation, drilling mud sampled from within a drill string, and drilling mud sampled from an annulus formed between the drill string and a borehole penetrating the subterranean formation. The means for obtaining the mass spectrum may be configured to obtain the mass spectrum downhole. The component concentration determining means may be configured to determine the concentration of the component downhole. The component concentration determining means may be configured to determine relative concentrations of a plurality of components of the composition of the sample utilizing the chemical and electron ionization model and the obtained mass spectrum. The mass spectrum obtaining means and the component concentration determining means may not utilize gas chromatography.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A method, comprising:

conveying a downhole tool in a borehole penetrating a subterranean formation;

obtaining, using the downhole tool while the downhole tool is positioned downhole, a mass spectrum of a sample subject to a combined chemical and electron ionization process; and determining a concentration of a component of the sample by utilizing a chemical and electron ionization model and the obtained mass spectrum.

2. The method of claim 1 wherein the sample is obtained downhole from a formation fluid sampled from the subterranean formation.

3. The method of clam 1 wherein the sample is obtained downhole from a drilling fluid sampled from within a drill string proximate the downhole tool.

4. The method of claim 1 wherein the sample is obtained downhole from a drilling fluid sampled from an annulus formed between a wall of the borehole and a drill string proximate the downhole tool.

5. The method of claim 1 wherein determining the concentration of the component is performed using the downhole tool while the downhole tool is positioned down hole.

6. The method of claim 1 wherein determining the concentration of the component comprises determining a proportion of the component relative to another component of the sample.

7. The method of claim 1 wherein the chemical and electron ionization model is linear in pressure.

8. The method of claim 1 wherein the chemical and electron ionization model is calibrated for primary and binary interactions of the component.

9. The method of claim 1 wherein the component comprises at least one hydrocarbon specie.

10. The method of claim 1 wherein the component comprises hydrogen sulfide.

11. The method of claim 1 wherein the component comprises carbon dioxide.

12. The method of claim 1 wherein the component comprises nitrogen.

13. The method of claim 1 wherein the component comprises hydrogen.

14. The method of claim 1 wherein the component comprises helium.

15. The method of claim 1 wherein the determining the concentration of the component comprises using an inversion model.

16. The method of claim 1 wherein determining the concentration of the component comprises determining a relative concentration of a plurality of components of the sample.

17. The method of claim 1 wherein the mass spectrum comprises peaks and the intensities of the peaks are used in the chemical and electron ionization model.

18. The method of claim 17 wherein a selected number of peaks are used in the chemical and electron ionization model.

19. The method of claim 1 wherein determining the concentration of the component is performed without separation of a plurality of components of the sample.

20. The method of claim 1 wherein at least one component of the sample is a chemical reagent.

* * * * *